US006790628B2

(12) United States Patent
Sarkar et al.

(10) Patent No.: US 6,790,628 B2
(45) Date of Patent: Sep. 14, 2004

(54) METHOD FOR SCREENING ANALOGS OF G-CSF

(75) Inventors: Casim A. Sarkar, Cambridge, MA (US); Douglas A. Lauffenburger, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/950,473

(22) Filed: Sep. 10, 2001

(65) Prior Publication Data

US 2002/0151488 A1 Oct. 17, 2002

Related U.S. Application Data

(60) Provisional application No. 60/231,464, filed on Sep. 8, 2000.

(51) Int. Cl.[7] .................... G01N 33/53; G01N 33/567

(52) U.S. Cl. ................. 435/7.21; 435/7.1; 435/7.2

(58) Field of Search ................. 435/7.1, 7.2, 7.21, 435/7.24

(56) References Cited

U.S. PATENT DOCUMENTS

| 4,810,643 A | 3/1989 | Souza |
| 4,904,584 A | 2/1990 | Shaw |
| 5,214,132 A | 5/1993 | Kuga et al. |
| 5,218,092 A | 6/1993 | Sasaki et al. |
| 5,581,476 A | 12/1996 | Osslund |
| 5,849,883 A | 12/1998 | Boone et al. |

FOREIGN PATENT DOCUMENTS

| AU | A-76380/91 | 11/1991 |
| AU | A-10948/92 | 8/1992 |
| EP | 0 243 153 | 10/1987 |
| EP | 0 256 843 | 2/1988 |
| EP | 0 272703 | 6/1988 |
| EP | 0 335 423 | 10/1989 |
| EP | 0 456 200 | 5/1991 |
| EP | 0 459 630 | 12/1991 |
| GB | 2 213 821 | 8/1989 |
| WO | WO 90/12874 | 11/1990 |

OTHER PUBLICATIONS

Watanabe et al. Analytical Biochem. 195, 38–44, 1991.*
International Search Report from the European Patent Office (International Search Authority) for PCT/US01/28828 (counterpart PCT application).
Lauffenburger et al., "Scratching the (cell) surface: cytokine engineering for improved ligand/receptor trafficking dynamics", Chem Biol 5:R257–R263, 1998.
French and Lauffenburger, "Controlling Receptor/Ligand Trafficking: Effects of Cellular and Molecular Properties on Endosomal Sorting", Ann Biomed Eng 25:690–707, 1997.

Vecchiarelli et al., "Beneficial Effect of Recombinant Human Granulocyte Colony–Stimulating Factor on Fungicidal Activity of Polymorphonuclear Leukocytes from Patients with AIDS", J Infect Dis 171: 1448–1454, 1995.
Fukunaga et al., "Growth and Differentiation Signals Mediated by Different Regions in the Cytoplasmic Domain of Granulocyte Colony–Stimulating Factor Receptor", Cell 74:1079–1087, 1993.
Welte et al., "Purification and biochemical characterization of human pluripotent hematopoietic colony–stimulating factor", Proc Natl Acad Sci USA 82:1526–1530, 1985.
Souza et al., "Recombinant Human Granulocyte Colony–Stimulating Factor: Effects on Normal and Leukemic Myeloid Cells", Science 232:61–65, 1986.
Gabrilove, "Introduction and Overview of Hematopoietic Growth Factors", Sem Hematol 26(2):1–14, 1989.
Wendel et al., "Granulocyte Colony–Stimulating Factor Treatment Protects Rodents Against Lipopolysaccharide–Induced Toxicity Via Suppression of Systemic Tumor Necrosis Factor", J Immunol 149:918–924, 1992.
Horan et al., "Dimerization of the Extracellular Domain of Granulocyte–Colony Stimulating Factor Receptor by Ligand Binding: A Monovalent Ligand Induced 2:2 Complexes", Biochemistry 35:4886–4896, 1996.
Horan et al., "Dimerization of Granulocyte–Colony Stimulating Factor Receptor: The lg Plus CRH Construct of Granulocyte–Colony Stimulating Factor Receptor Forms a 2:2 Complex with a Ligand", J Biochem 121:370–375, 1997.
Fukunaga et al., "Functional domains of the granuloctye colony–stimulating factor receptor", EMBO J 10:2855–2865, 1991.
Aritomi et al., Atomic structure of the GCSF–receptor complex showing a new cytokine–receptor recognition scheme, Nature 401:713–717, 1999.
Jones et al., "Growth factors in haemopoiesis", Bailliere's Clin Hematol 2(1):83–111, 1989.
Nagata et al., "The chromosomal gene structure and two mRNAs for human granulocyte colony–stimulating factor", EMBO J 5:575–581, 1986.
Moore et al., "Synergy of interleukin 1 and granulocyte colony–stimulating factor: In Vivo stimulation of stem cell recovery and hematopoietic regeneration following 5–fluorouracil treatment of mice", Proc Natl Acad Sci USA 84:7134–7138, 1987.

(List continued on next page.)

Primary Examiner—Prema Mertz
(74) Attorney, Agent, or Firm—Marshall, Gerstein & Borun LLP

(57) ABSTRACT

The present invention relates to granulocyte colony stimulating factor ("G-CSF") polypeptide analog compositions. The concept detailed herein provides methods for screening G-CSF analogs, designed with one or more substitutions to amino acids, and selecting analogs for use as G-CSF replacements or antagonists, and may be generalizable beyond G-CSF analogs as well. In addition, pharmaceutical compositions and methods of use are provided for analogs so selected.

5 Claims, 1 Drawing Sheet

OTHER PUBLICATIONS

Diflo et al., "ASSLD Abstract of Papers", *Hepatology* 16:PA278, 1992.

Wright et al., "Abstracts of Papers Submitted to the American Association for the Study of Liver Diseases", *Hepatology* 14:PA48, 1991.

Lachaux et al., "Treatment with lenograstim (glycosylated recombinant human granulocyte colony–stimulating factor) and orthotopic liver transplantation for glycogen storage disease type lb", *J Ped* 123:1005–1008, 1993.

Colquehoun et al., "Reversal of Neutropenia with Granulocyte Colony–Stimulating Factor Without Precipitating Liver Allograft Rejection", *Transplantation* 56:755–758, 1993.

Kuga et al., "Mutagenesis of human granulocyte colony stimulating factor", *Biochem Biophys Res Comm* 159:103–111, 1989.

Lu et al., Disulfide and Secondary Structures of Recombinant Human Granulocyte Colony Stimulating Factor, *Arch Biochem Biophys* 268:81–92, 1989.

Okabe et al., "In Vitro and In Vivo Hematopoietic Effect of Mutant Human Granulocyte Colony–Stimulating Factor", *Blood* 75(9):1788–1793, 1990.

Kuwubara et al., "Receptor–mediated clearance of G–CSF derivative nartograstim in bone marrow of rats", *Amer J Physiol Endocrinol Metabol* 32:E1–E9, 1995.

Wiley et al., "The Endocytotic Rate Constant: A Cellular Parameter for Quantitating Receptor–Mediated Endocytosis", *J Biol Chem* 257:4222–4229, 1982.

* cited by examiner

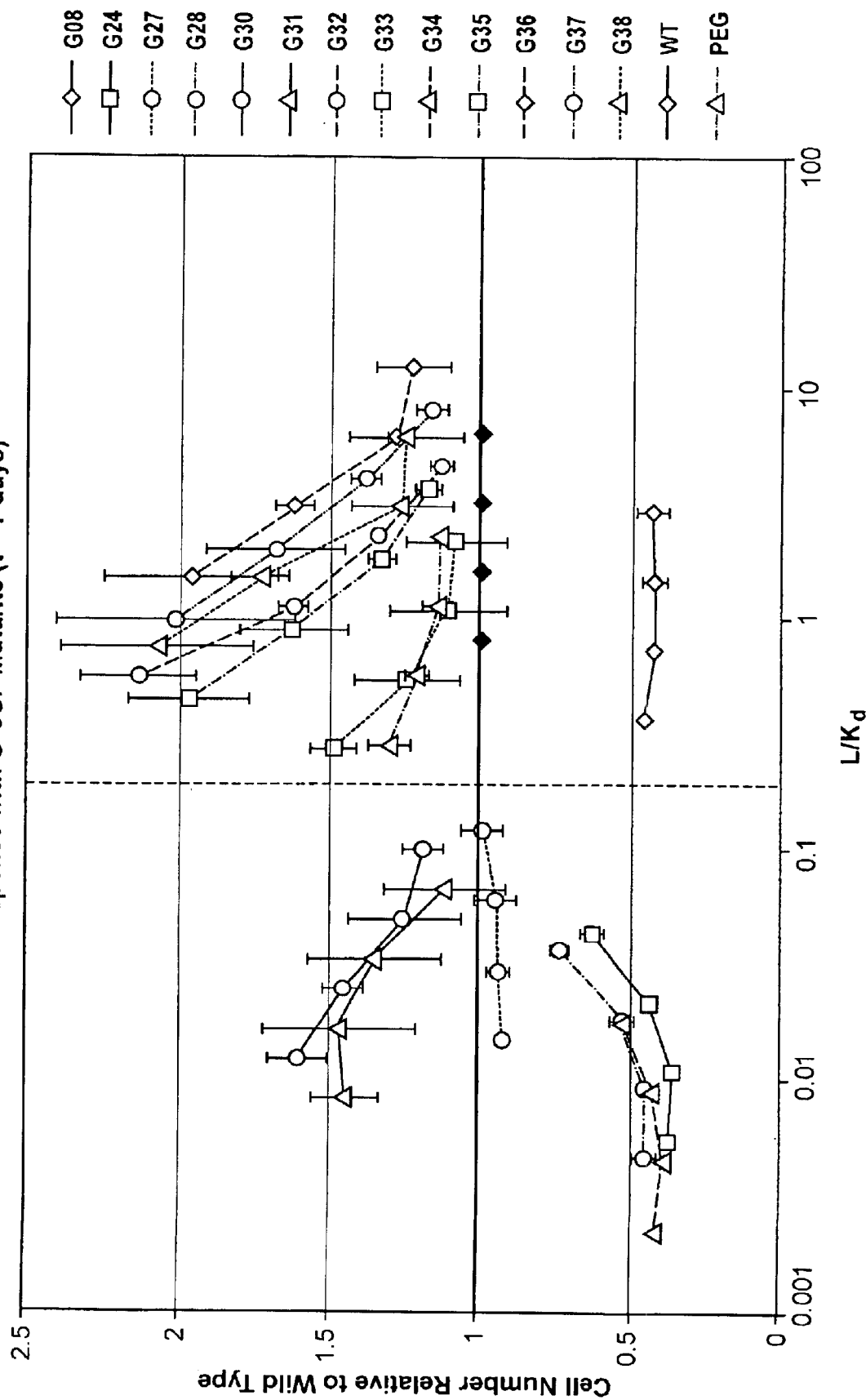

METHOD FOR SCREENING ANALOGS OF G-CSF

This application claims benefit of U.S. Provisional Application Ser. No. 60/231,464 filed Sep. 8, 2000, which is incorporated herein by reference in its entirety.

FIELD OF THE INVENTION

The present invention relates to granulocyte colony stimulating factor ("G-CSF") polypeptide analog compositions, related nucleic acids, and vectors, host cells and processes for recombinant DNA production of the G-CSF analog polypeptides. More particularly the invention provides methods for screening G-CSF analogs, designed with one or more substitutions to amino acids, and selecting analogs for use as G-CSF replacements or antagonists. In addition, pharmaceutical compositions and methods of use are provided for analogs so selected.

BACKGROUND OF THE INVENTION

Many therapeutic ligands elicit cellular responses by binding to cell-surface receptors to elicit cellular responses. Drug design is typically focused on the ability of a ligand to bind tightly and specifically to its intended target. However, if the drug is a protein and the target a cell-surface receptor, there are additional issues to consider from a systems-level analysis. When therapeutic ligands bind to receptors on the surface of a cell, an intracellular signaling cascade is initiated that ultimately results in an appropriate cellular response. Additionally, modulation—generally attenuation—of these signals begins almost immediately by cellular trafficking of the ligand-receptor complexes. The complexes on the surface of the cell are internalized into vesicles that fuse with endosomal compartments. From endosomes, the molecules can either be routed to degradation in lysosomes or be recycled to the cell surface intact, where free and ligand-bound receptor are redisplayed and free ligand is released to the extracellular medium. Recent evidence suggests the outcome of this sorting decision for complexes involving growth factors or cytokines often is related to the endosomal affinity constant for the ligand-receptor interaction: complexes that remain bound are readily degraded while those that dissociate are recycled [Lauffenburger et al., Chem. Biol. 5:R257–R263 (1998)]. In general, dissociation of complexes in endosomes appears to enhance receptor recycling, because it results in altered interactions between the receptors and endosomal retention components.

Additionally, for a low number of intracellular complexes, which is the case for many clinically important cytokine-receptor systems, modeling indicates a particularly strong positive correlation between the inverse endosomal affinity and the fraction of ligand recycled [French and Lauffenburger, Ann. Biomed. Eng. 25:690–707 (1997)]. Thus, if a ligand could be designed to enhance endosomal dissociation after binding to and generating signals within its target cell, the drug might reduce receptor downregulation, so that cells would be more responsive to further ligand stimulation. The lifetime and effectiveness of the drug might also be enhanced if ligand recycling were augmented by endosomal dissociation. This contrasts with the conventional approach of attempting to improve ligand potency through enhanced affinity. If extracellular affinity enhancements extend to endosomes, such attempts might actually be counterproductive because they increase receptor downregulation and possibly ligand depletion. Thus, cellular trafficking may be a bottleneck in enhancing ligand potency, particularly in cases where degradation through receptor-mediated endocytosis is significant.

A system in which the optimization of cellular trafficking properties could have a profound impact on potency is that of granulocyte colony-stimulating factor (G-CSF) and its receptor (G-CSFR). G-CSF is a 19-kDa cytokine, which is one of the hematopoietic growth factors, also called colony stimulating factors. G-CSF is used to increase white blood cell (neutrophil) counts when blood levels of such cells are dangerously low. This commonly occurs when certain antibiotics, anti-HIV therapies and/or chemotherapies suppress the bone marrow. A recent study documents that G-CSF not only increases the number of neutrophils in the blood, but enhances the functional killing abilities of those cells as well [Vecchiarelli et al., J. Infect. Dis. 171:1448–1454 (1995)]. G-CSF specifically stimulates the proliferation and differentiation of neutrophilic precursor cells into mature neutrophils [Fukunaga et al., Cell 74:1079–1087 (1993)], and is useful for treating in neutropenic states [Welte et al., Proc. Natl. Acad. Sci. USA 82:1526–1530 (1985); Souza et al., Science 232:61–65 (1986); Gabrilove, Sem. Hematol. 26(2):1–14 (1989)]. G-CSF increases the number of circulating granulocytes and has been reported to ameliorate infection in sepsis models. G-CSF administration also inhibits the release of tumor necrosis factor (TNF), a cytokine important to tissue injury during sepsis and rejection [Wendel et al., J Immunol. 149:918–924 (1992)]. G-CSF is a member of the Group I superfamily of cytokines, characterized by an antiparallel 4-helical bundle structure and including other therapeutically important drugs such as erythropoietin and growth hormone. G-CSF binds specifically and with high affinity (apparent $K_D$~100 pM)[Morstyn, Dexter, & Foote (eds.) Filgrastim (r-metHuG-CSF) in: Clinical Practice, Edn. 2., Marcel Dekker, Inc., New York (1998)] to G-CSFR, resulting in a ligand:receptor complex with a 2:2 stoichiometry [Horan et al., Biochemistry 35:4886–4896 (1996); Horan et al., J. Biochem.121:370–375 (1997)]. The extracellular region of G-CSFR contains the ligand-binding cytokine receptor homology (CRH) domain [Fukunaga et al., EMBO J. 10:2855–2865 (1991)] and recently, the crystal structure of G-CSF complexed with the CRH domain of G-CSFR was solved, showing the expected 2:2 ligand:receptor stoichiometry [Aritomi et al., Nature, 401:713–717 (1999)].

In humans, endogenous G-CSF is detectable in blood plasma [Jones et al., Bailliere 's Clin. Hematol. 2(1):83–111 (1989)]. G-CSF is produced by fibroblasts, macrophages, T cells, trophoblasts, endothelial cells, and epithelial cells, and is the expression product of a single copy gene comprised of four exons and five introns located on chromosome seventeen. Transcription of this locus produces a mRNA species which is differentially processed, resulting in two forms of G-CSF mRNA, one version coding for a protein of 177 amino acids, the other coding for a protein of 174 amino acids [Nagata et al., EMBO J. 5:575–581 (1986)]. The form comprised of 174 amino acids has been found to have specific in vivo biological activity. SEQ ID NO: 1 presents a DNA encoding the 174 amino acid species of G-CSF and the corresponding sequence of amino acids is set out in SEQ ID NO: 2. G-CSF is species cross-reactive, such that when human G-CSF is administered to another mammal such as a mouse, canine, or monkey, sustained neutrophil leukocytosis is elicited [Moore et al., Proc. Natl. Acad. Sci. USA 84:7134–7138 (1987)].

Human G-CSF can be obtained and purified from a number of sources. Natural human G-CSF can be isolated from the supernatants of cultured human tumor cell lines. The development of recombinant DNA technology has enabled the production of commercial scale quantities of G-CSF in glycosylated form as a product of eukaryotic host cell expression, and of G-CSF in non-glycosylated form as a product of prokaryotic host cell expression. See, for example, U.S. Pat. No. 4,810,643 (Souza) incorporated herein by reference.

G-CSF has been found to be useful in the treatment of indications where an increase in neutrophils will provide benefits. For example, for cancer patients, G-CSF is beneficial as a means of selectively stimulating neutrophil production to compensate for hematopoietic deficits resulting from chemotherapy or radiation therapy. Other indications include treatment of various infectious diseases and related conditions, such as sepsis, which is typically caused by a metabolite of bacteria. G-CSF is also useful alone, or in combination with other compounds, such as other cytokines, for growth or expansion of cells in culture (for example, for bone marrow transplants or ex vivo expansion). G-CSF has been administered to transplant patients as an adjunct to treatment of infection or for treatment of neutropenia [Diflo et al., *Hepatology* 16:PA278 (1992); Wright et al., *Hepatology* 14:PA48 (1991); Lachaux et al., *J. Ped.* 123:1005–1008 (1993); Colquehoun et al., *Transplantation* 56:755–758 (1993)]. However, G-CSF is rapidly cleared through receptor-mediated endocytosis by peripheral neutrophils and precursor cells in bone marrow expressing G-CSFR [Morstyn, Dexter, & Foote (eds.) Filgrastim (r-metHuG-CSF) in: *Clinical Practice*, Edn. 2., Marcel Dekker, Inc., New York (1998)]. Thus, the potency of the drug is reduced by this negative feedback mechanism. Since cells naturally express G-CSFR in low numbers, decreasing the endosomal affinity of the complex may not only reduce receptor downregulation but may also enhance ligand recycling, as predicted by modeling [French and Lauffenburger, *Ann. Biomed. Eng.* 25:690–707 (1997)]. Therefore, G-CSF is a prime candidate for mutagenesis to enhance trafficking properties, thereby improving drug potency.

Various altered G-CSF's have been reported. Generally, for design of drugs, certain changes are known to have certain structural effects. For example, deleting one cysteine could result in the unfolding of a molecule which, in its unaltered state, is normally folded via a disulfide bridge. There are other known methods to one skilled in the art for adding, deleting or substituting amino acids in order to change the function of a protein.

Recombinant human G-CSF mutants have been prepared, but the method of preparation does not include overall structure/function relationship information. For example, the mutation and biochemical modification of Cys 18 has been reported [Kuga et al., *Biochem. Biophy. Res. Comm.* 159:103–111 (1989); Lu et al., *Arch. Biochem. Biophys.* 268:81–92 (1989)].

In U.S. Pat. No. 4,810,643, entitled, "Production of Pluripotent Granulocyte Colony-Stimulating Factor" (incorporated by reference herein), polypeptide analogs and peptide fragments of G-CSF are disclosed generally. Specific G-CSF analogs disclosed include those with the cysteines at positions 17, 36, 42, 64, and 74 (of the 174 amino acid species or of those having 175 amino acids, the additional amino acid being an N-terminal methionine) substituted with another amino acid (such as serine), and G-CSF with an alanine in the first (N-terminal) position.

EP 0 335 423 entitled "Modified human G-CSF" reportedly discloses the modification of at least one amino group in a polypeptide having hG-CSF activity.

EP 0 272 703 entitled "Novel Polypeptide" reportedly discloses G-CSF derivatives having an amino acid substituted or deleted at or "in the neighborhood" of the N-terminus. Also, Okabe et al. [*Blood* 75(9):1788–1793 (1990)], reportedly discloses modifications of five positions of the N-terminal region of human G-CSF.

EP 0 459 630, entitled "Polypeptides" reportedly discloses derivatives of naturally occurring G-CSF having at least one of the biological properties of naturally occurring G-CSF and a solution stability of at least 35% at 5 mg/mL in which the derivative has at least $Cys^{17}$ of the native sequence replaced by a $Ser^{17}$ residue and $Asp^{27}$ of the native sequence replaced by a $Ser^{27}$ residue.

EP 0 256 843 entitled "Expression of G-CSF and Muteins Thereof and Their Uses" reportedly discloses a modified DNA sequence encoding G-CSF wherein the N-terminus is modified for enhanced expression of protein in recombinant host cells, without changing the amino acid sequence of the protein.

EP 0 243 153 entitled "Human G-CSF Protein Expression" reportedly discloses G-CSF to be modified by inactivating at least one yeast KEX2 protease processing site for increased yield in recombinant production using yeast.

Shaw, U.S. Pat. No. 4,904,584, entitled "Site-Specific Homogeneous Modification of Polypeptides" reportedly discloses lysine altered proteins.

WO/9012874 reportedly discloses cysteine altered variants of proteins.

Australian Patent Application Document No. AU-A-10948/92, entitled, "Improved Activation of Recombinant Proteins" reportedly discloses the addition of amino acids to either terminus of a G-CSF molecule for the purpose of aiding in the folding of the molecule after prokaryotic expression.

Australian Patent Application Document No. AU-A-76380/91, entitled, "Muteins of the Granulocyte Colony Stimulating Factor (G-CSF)" reportedly discloses muteins of G-CSF in the sequence Leu-Gly-His-Ser-Leu-Gly-Ile at position 50–56 of G-CSF with 174 amino acids, and position 53 to 59 of the G-CSF with 177 amino acids, and/or at least one of the four histidine residues at positions 43, 79, 156 and 170 of the mature G-CSF with 174 amino acids or at positions 46, 82, 159, or 173 of the mature G-CSF with 177 amino acids.

GB 2 213 821, entitled "Synthetic Human Granulocyte Colony Stimulating Factor Gene" reportedly discloses a synthetic G-CSF-encoding nucleic acid sequence incorporating restriction sites to facilitate the cassette mutagenesis of selected regions, and flanking restriction sites to facilitate the incorporation of the gene into a desired expression system.

U.S. Pat. No. 5,214,132 reportedly discloses the modification of human G-CSF at amino acid positions 1, 3, 4, 5,and 17 [see, also, Kuga et al., *Biochem. Biophys. Res. Commun.* 159:103–111 (1989)].

U.S. Pat. No. 5,218,092 reportedly discloses the modification of human G-CSF at amino acid positions 1, 3, 4, 5, 17, 145, and 147.

U.S. Pat. No. 5,581,476 (incorporated by reference herein) discloses the three-dimensional structure of G-CSF to the atomic level. From this three-dimensional structure, one can forecast with substantial certainty how changes in the composition of a G-CSF molecule may result in structural changes. These structural characteristics may be correlated with biological activity to design and produce G-CSF analogs.

Signal transduction, the way in which G-CSF affects cellular metabolism, is not currently thoroughly understood. In general, G-CSF binds to and activates the G-CSF cell-surface receptor through conformational changes. This binding thereby initiates a signaling cascade (e.g., recruiting kinases to the cytoplasmic domain) which apparently initiates the changes within particular progenitor cells, leading to cellular responses such as differentiation, proliferation and migration. The G-CSF/G-CSFR complex is thought to undergo endocytic trafficking processes of internalization and sorting to recycling or degradation [Lauffenburger, and Linderman, *Receptors: Models for Binding, Trafficking, and Signaling*, New York: Oxford University Press (1993)].

Endocytic uptake of G-CSF potentiates intracellular proteolytic cytokine degradation in endosomal and/or lysosomal compartments. Internalized cytokine receptors if not recycled can be destroyed. Thus, endocytic trafficking could cause the depletion of G-CSF from the extracellular medium, as well as the downregulation of the G-CSF receptor. Accordingly, it would be beneficial to alter the G-CSF structure in a manner that retains proper receptor activation for signal transduction, but diminishes endocytic internalization and/or enhances endosomal sorting to recycling rather than degradation [Lauffenburger et al., Scratching The (Cell) Surface: Cytokine Engineering For Improved Ligand/Receptor Trafficking Dynamics, *Chem & Biol* 5:R257–R263 (1988)].

Thus, there is a need to develop better therapeutic ligands of G-CSF. Such agents would have longer half-lives and induce greater cellular proliferation if the ligand were not as prone to endocytosis and subsequent lysosomal degradation. Accordingly, it is an object of the present invention to provide these ligands and methods for producing and testing them.

SUMMARY OF THE INVENTION

The present invention provides methods of screening G-CSF amino acid substitution analogs based upon their binding affinities for the G-CSF receptor along with their ability to increase or decrease myeloid cell proliferation and thereby to assess affects on cellular trafficking and, thus, identify G-CSF analogs for use as G-CSF replacements or G-CSF antagonists.

In one aspect, therefore, the present invention relates a method for screening analogs of G-CSF for use as G-CSF replacements. This method comprises: determining the capacity of the G-CSF analog for binding to target cells and determining an equilibrium dissociation constant (Kd) for said analog; determining the capacity of the G-CSF analog for stimulating cellular proliferation (N) of target cells at a given initial ligand concentration (L); normalizing the N value obtained for the G-CSF analog with the corresponding N value for wild-type G-CSF at a given value of L to obtain Y-axis values; calculating the L/Kd values for the G-CSF analog and wild-type G-CSF to obtain X-axis values; plotting the normalized N value with the L/Kd values for the G-CSF analog and wild-type G-CSF; selecting as a G-CSF replacement, an analog displaying increased proliferation and either increased or decreased binding relative to wild-type G-CSF. As used herein, "wild-type G-CSF" shall mean and include the 174 amino acid species of human G-CSF set out in SEQ ID NO: 2 as well as the $Met^{-1}$ species thereof.

In another aspect, the present invention relates a method for screening analogs of G-CSF for use as G-CSF antagonists. This method comprises: determining the capacity of the G-CSF analog for binding to target cells and determining an equilibrium dissociation constant (Kd) for said analog; determining the capacity of the G-CSF analog for stimulating cellular proliferation (N) of target cells at a given initial ligand concentration (L); normalizing the N value obtained for the G-CSF analog with the corresponding N value for wild-type G-CSF at a given value of L to obtain Y-axis values; calculating the L/Kd values for the G-CSF analog and wild-type G-CSF to obtain X-axis values; plotting the normalized N value with the L/Kd values for the G-CSF analog and wild-type G-CSF; and selecting as a G-CSF antagonist an analog displaying decreased proliferation and either equal or greater binding relative to wild-type G-CSF.

Assessment of cellular proliferation, according to the invention, preferably involves determining cell number, measuring $^3$H-thymidine incorporation, or using an MTT assay. Furthermore, the equilibrium dissociation constant (Kd), as described herein, is preferably assessed by BIAcore analysis or ELISA.

Another aspect of the invention provides a method of treating a hematopoietic, neurological or reproduction related conditions comprised of administering an effective amount of a G-CSF replacement selected according to the method as described herein, illustrated by the exemplary analogs $[Glu^{50}]$G-CSF, $[Glu^{54}]$G-CSF, $[Ala^{33}]$G-CSF, $[Glu^{26}]$G-CSF, $[Asp^{30}]$G-CSF, $[Leu^{26}]$G-CSF, $[Ala^{38}]$G-CSF, $[Ala^{26}]$G-CSF, and the $Met^{-1}$ species thereof.

An additional aspect of the invention provides a method of treating neutrophilia comprised of administering an effective amount of a G-CSF antagonist selected according to the method as described herein, illustrated by the exemplary analog $[Ala^{46}]$G-CSF, and the $Met^{-1}$ species thereof.

The invention also provides a method of treating a hematopoietic, neurological or reproduction related conditions wherein said condition is selected from the group consisting of: reduced hematopoietic function, reduced immune function, reduced neutrophil count, reduced neutrophil mobilization, mobilization of peripheral blood progenitor cells, sepsis, severe chronic neutropenia, bone marrow transplants, infectious diseases, leucopenia, thrombocytopenia, anemia, enhancing engraftment of bone marrow during transplantation, enhancing bone marrow recovery in treatment of radiation, chemical or chemotherapeutic induced bone marrow aplasia or myelosuppression, and acquired immune deficiency syndrome.

The invention further comprehends a method of sensitizing cells to chemotherapy and radiotherapy comprised of administering an effective amount of a G-CSF replacement selected according to the method as described herein.

In yet another aspect, the invention provides a method for culturing hematopoietic cells in vitro comprising: placing said cells in a suitable culture medium, said suitable culture medium containing a G-CSF replacement selected according to the method as described herein; and providing suitable conditions for the growth of said hematopoietic cells.

The invention further provides a method wherein said treatment, sensitizing, or culturing includes the use of at least one additional factor selected from among EPO, G-CSF, SCF, M-GDF, GM-CSF, M-CSF, CSF-1, IL-1, IL-2, IL-3, IL-4, IL-5, IL-6, IL-7, IL-8, IL-9, IL-10, IL-11, IL-12, interleukins, IGF-1, LIF, interferon, a neurotrophic factor, flt-3/flk-2 ligand, and a fibroblast growth factor.

An additional aspect of the invention provides a kit containing components for culturing hematopoietic cells comprised of: any of the polypeptide analogs selected according to the methods as described herein; components suitable for preparing medium for culturing hematopoietic cells; and, optionally, at least one additional factor as set out above.

In yet another aspect, the target cell, as described herein, is preferably a bone marrow stem cell, a neutrophil precursor cell, an immortalized stem cell, or an acute myeloid leukemia cell.

In still another aspect, the invention provides a method of treating a hematopoietic, neurological or reproduction related conditions comprised of administering an effective amount of any of the G-CSF replacements screened according to the invention, illustratively analogs selected from the group consisting of: [Glu$^{50}$]G-CSF, [Glu$^{54}$]G-CSF, [Ala$^{33}$]G-CSF, [Glu$^{26}$]G-CSF, [Asp$^{30}$]G-CSF, [Leu$^{26}$]G-CSF, [Ala$^{38}$]G-CSF, [Ala$^{26}$]G-CSF, and the Met$^{-1}$ species thereof.

Alternately, the invention provides a method of treating neutrophilia comprised of administering an effective amount of [Ala$^{46}$]G-CSF and the Met$^{-1}$ species thereof.

The invention also provides a method of sensitizing cells to chemotherapy and radiotherapy comprised of administering an effective amount of any of the G-CSF replacements screened according to the invention, illustratively analogs selected from the group consisting of: [Glu$^{50}$]G-CSF, [Glu$^{54}$]G-CSF, [Ala$^{33}$]G-CSF, [Glu$^{26}$]G-CSF, [Asp$^{30}$]G-CSF, [Leu$^{26}$]G-CSF, [Ala$^{38}$]G-CSF, [Ala$^{26}$]G-CSF, and the Met$^{-1}$ species thereof.

In another aspect, the invention provides a method for culturing hematopoietic cells in vitro comprising: placing said cells in a suitable culture medium, said suitable culture medium containing a G-CSF replacement screened according to the invention, illustratively analogs selected from the group consisting of: [Glu$^{50}$]G-CSF, [Glu$^{54}$]G-CSF, [Ala$^{33}$]G-CSF, [Glu$^{26}$]G-CSF, [Asp$^{30}$]G-CSF, [Leu$^{26}$]G-CSF, [Ala$^{38}$]G-CSF, [Ala$^{26}$]G-CSF, and the Met$^{-1}$ species thereof; and providing suitable conditions for the growth of said hematopoietic cells.

Furthermore, the invention provides a method wherein said treatment, sensitizing, or culturing with the aforementioned G-CSF analogs includes the use of at least one additional factor selected from among EPO, G-CSF, SCF, M-GDF, GM-CSF, M-CSF, CSF-1, IL-1, IL-2, IL-3, IL-4, IL-5, IL-6, IL-7, IL-8, IL-9, IL-10, IL-11, IL-12, interleukins, IGF-1, LIF, interferon, a neurotrophic factor, flt-3/flk-2 ligand, and a fibroblast growth factor.

The invention further comprehends a kit containing components for culturing hematopoietic cells comprised of: any of the G-CSF analogs screened according to the invention, illustratively analogs selected from the group consisting of: [Glu$^{50}$]G-CSF, [Glu$^{54}$]G-CSF, [Ala$^{33}$]G-CSF, [Glu$^{26}$]G-CSF, [Asp$^{30}$]G-CSF, [Leu$^{26}$]G-CSF, [Ala$^{38}$]G-CSF, [Ala$^{26}$]G-CSF, [Ala$^{46}$]G-CSF, and the Met$^{-1}$ species thereof; components suitable for preparing medium for culturing hematopoietic cells; and, optionally, at least one additional factor as set out above.

BRIEF DESCRIPTION OF THE DRAWING

FIG. 1 demonstrates a plot of one of the methods of the invention, demonstrating cellular proliferation and binding activity of several G-CSF analogs in relation to wild-type G-CSF.

DETAILED DESCRIPTION OF THE INVENTION

G-CSF has been found to be useful in the treatment of various conditions where an increase in neutrophils will provide benefits. For example, for cancer patients, G-CSF is beneficial as a means of selectively stimulating neutrophil production to compensate for hematopoietic deficits resulting from chemotherapy or radiation therapy. Other indications include treatment of various infectious diseases and related conditions, such as sepsis, which is typically caused by a metabolite of bacteria. G-CSF is also useful alone, or in combination with other compounds, such as other cytokines, for growth or expansion of cells in culture (for example, for bone marrow transplants or ex vivo expansion). G-CSF has been administered to transplant patients as an adjunct to treatment of infection or for treatment of neutropenia. However, it is rapidly cleared through receptor-mediated endocytosis by peripheral neutrophils and precursor cells in bone marrow expressing G-CSFR, and thus, the potency of the drug is reduced by this negative feedback mechanism. Because cells naturally express G-CSFR in low numbers, decreasing the endosomal affinity of the complex may not only reduce receptor downregulation but may also enhance ligand recycling, as predicted by modeling. Therefore, G-CSF drug potency would be improved by mutations to G-CSF that would enhance trafficking properties.

The present invention describes novel G-CSF analog polypeptides which demonstrate advantages in stability which are not seen in other G-CSF species. In particular, these analogs are those that provide enhanced cellular response (superagonist or G-CSF agonist type activity) as compared to G-CSF or metG-CSF. Such changes in cellular response can occur by affecting G-CSF receptor binding and/or the processes of sorting, recycling and degradation via the ligand/receptor endocytic trafficking pathways.

All analog changes of the present invention are based on the 174 amino acid sequence for G-CSF in SEQ ID NO: 2. One skilled in the art will appreciate that the analogs of the present invention may also be constructed with an N-terminal methionine residue.

The section headings are used herein for organizational purposes only, and are not to be construed as in any way limiting the subject matter described.

A. Role of G-CSF in the Treatment of Neutropenia

G-CSF has been found to be useful in the treatment of conditions where an increase in neutrophils will provide benefits. For example, for cancer patients, G-CSF is beneficial as a means of selectively stimulating neutrophil production to compensate for hematopoietic deficits resulting from chemotherapy or radiation therapy. Other indications include treatment of various infectious diseases and related conditions, such as sepsis, which is typically caused by a metabolite of bacteria. G-CSF is also useful alone, or in combination with other compounds, such as other cytokines, for growth or expansion of cells in culture (for example, for bone marrow transplants or ex vivo expansion). G-CSF has been administered to transplant patients as an adjunct to treatment of infection or for treatment of neutropenia [Diflo et al., *Hepatology* 16:PA278 (1992); Wright et al., *Hepatology* 14:PA48 (1991); Lachaux et al., *J. Ped.* 123:1005–1008 (1993); Colquehoun et al., *Transplantation* 56:755–758 (1993)].

The term "neutropenia" refers to a condition with an abnormally low number of neutrophils in the peripheral circulation. The neutrophil arises from the bone marrow and is fully mature when it is released into the circulation. It is then fully prepared to function in its role as the first line of cellular defense. It becomes activated, i.e., able to perform many of its functions, by exposing it to certain pro-inflammatory mediators and the chemotactic factors that attract it to the site of an inciting stimulus. Severe neutropenia can be life-threatening, because it can lead to severe infections.

Alternately, the term "neutrophilia" refers to a condition with an abnormally high number of neutrophils in the peripheral circulation. Neutrophilia, or an increased white blood count, has many causes, including exposure to extreme cold, heat, recent surgery, physical trauma, infection of any type, burns, shocks, tumors, non-infection inflammation, such as gout, arthritis, thyroid problems, and drugs.

B. G-CSF Analogs of the Present Invention

In one embodiment, the present invention provides three G-CSF analog polypeptides and corresponding nucleic acids containing: 1) glutamic acid substituted for leucine at position 50, [Glu$^{50}$]G-CSF; 2) alanine substituted for glutamic acid at position 46, [Ala$^{46}$]G-CSF; 3) alanine substituted for glutamic acid at position 33, [Ala$^{33}$]G-CSF; (all according to the numbering of SEQ ID NO: 2, where methionine is at position −1).

Additional test analogs of the present invention include: 1) glutamic acid substituted for phenylalanine at position 144, [Glu$^{144}$]G-CSF; 2) glutamic acid substituted for leucine at position 41, [Glu$^{41}$]G-CSF; 3) glutamic acid substituted for leucine at position 47, [Glu$^{47}$]G-CSF; 4 glutamic acid substituted for leucine at position 54, [Glu$^{54}$]G-CSF; 5) glutamic acid substituted for glycine at position 26, [Glu$^{26}$]G-CSF; 6) alanine substituted for glutamic acid at position 19, [Ala$^{19}$]G-CSF; 7) aspartic acid substituted for alanine at position 30, [Asp$^{30}$]G-CSF; 8) leucine substituted for glycine at position 26, [Leu$^{26}$]G-CSF; 9) alanine substituted for threonine at position 38, [Ala$^{38}$]G-CSF; and 10) alanine substituted for glycine at position 26, [Ala$^{26}$]G-CSF. The above substitutions are also according to the numbering of SEQ ID NO: 2, where methionine is at position −1.

By human G-CSF analog polypeptides, the present invention means human G-CSF in which the wild-type G-CSF sequence has been mutated. The present invention contemplates the production, assessment, and selection of human G-CSF analog polypeptides that have an increased potency relative to wild-type G-CSF to stimulate cellular proliferation, and increased half-lives. Such changes in cellular response occur by affecting G-CSF receptor binding and/or the processes of sorting, recycling, and degradation via the ligand/receptor endocytic trafficking pathways.

Substitutions

Specifically contemplated by the present invention is site-specific mutagenesis of wild-type G-CSF. While the amino acid sequence variants of the polypeptide can be substitutional mutants in which the amino acid at a given site is substituted for another, insertional or deletion variants also are contemplated.

Substitutional variants typically exchange one amino acid of the wild-type for another at one or more sites within the protein, and may be designed to modulate one or more properties of the polypeptide, such as stability against proteolytic cleavage, without the loss of other functions or properties. Substitutions of to maintain activity or properties preferably are conservative, that is, one amino acid is replaced with one of similar shape and charge.

Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in the Table A (from WO 97/09433, page 10, published Mar. 13, 1997 (PCT/GB96/02197, filed Sep. 6, 1996), immediately below.

TABLE A

| Conservative Substitutions I | |
|---|---|
| SIDE CHAIN CHARACTERISTIC | AMINO ACID |
| Aliphatic | |
| Non-polar | G A P |
| | I L V |
| Polar-uncharged | C S T M |
| | N Q |
| Polar-charged | D E |
| | K R |
| Aromatic | H F W Y |
| Other | N Q D E |

Alternatively, conservative amino acids can be grouped as described in Lehninger, [*Biochemistry*, Second Edition; Worth Publishers, Inc. NY:N.Y. (1975), pp.71–77] as set out in Table B, immediately below.

TABLE B

| Conservative Substitutions II | |
|---|---|
| SIDE CHAIN CHARACTERISTIC | AMINO ACID |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still an another alternative, exemplary conservative substitutions are set out in Table C, immediately below.

TABLE C

| Conservative Substitutions III | |
|---|---|
| Original Residue | Exemplary Substitution |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |

TABLE C-continued

Conservative Substitutions III

| Original Residue | Exemplary Substitution |
| --- | --- |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

Also contemplated are non-conservative substitutions, in which an amino acid is replaced with one of different properties.

In order to construct G-CSF analogs such as those described herein, one of skill in the art may employ well known standard chemical synthesis and recombinant technologies.

The present invention also contemplates nucleic acids encoding the present G-CSF analogs. Novel nucleic acid sequences of the invention include sequences useful in securing protein expression in procaryotic or eucaryotic host cells. The nucleic acids may be purified and isolated, so that the desired coding region is useful to produce the present polypeptides.

These DNA sequences may incorporate codons facilitating transcription and translation of mRNA in microbial hosts. Such manufacturing sequences may readily be constructed according to the methods well known in the art. See, also, Alton et al., PCT published application WO 83/04053. The DNAs above may also optionally encode an N-terminal methionyl residue.

DNA sequences provided by the invention are useful in generating new and useful viral and plasmid DNA vectors, new and useful transformed and transfected procaryotic and eucaryotic host cells (including bacterial, yeast, and mammalian cells grown in culture), and new and useful methods for cultured growth of such host cells capable of expression of the present G-CSF analogs. The DNA sequences encoding biologically active G-CSF analogs herein (or corresponding RNAs) may be useful for gene therapy in instances where underproduction of G-CSF would be alleviated, or the need for increased levels of G-CSF.

The present invention also provides for processes for recombinant DNA production of the present G-CSF analogs. Provided is a process for producing the G-CSF analogs from a host cell containing nucleic acid encoding such analogs comprised of: a) culturing said host cell containing nucleic acid encoding such G-CSF analogs under conditions facilitating the expression of such DNA molecule; and b) obtaining such G-CSF analogs.

One may optionally purify and isolate such G-CSF analogs from other components obtained in the process. Methods for purifying can be found in U.S. Pat. No. 5,849,883 (incorporated by reference herein). Other methods are well known in the art (See, also, Souza, supra).

Host cells may be prokaryotic or eukaryotic and include bacteria, mammalian cells (such as Chinese Hamster Ovary (CHO) cells, monkey cells, baby hamster kidney cells, cancer cells or other cells), yeast cells, and insect cells. Preferred for greatest ease in commercial production is production using a bacterial host cell.

C. Protein Production

Given the above disclosure of human G-CSF analog polypeptides, it will be possible for one of skill in the art to produce human G-CSF analog polypeptides by automated peptide synthesis, by recombinant techniques or both.

The human G-CSF analogs of the invention can be synthesized in solution or on a solid support in accordance with conventional techniques. Various automatic synthesizers are commercially available and can be used in accordance with known protocols. See, for example, Stewart and Young, Solid Phase Peptide Synthesis, 2d. ed., Pierce Chemical Co. (1984);Tam et al., J. Am. Chem. Soc. 105:6442 (1983); Merrifield, Science 232: 341–347 (1986); and Barany and Merrifield, The Peptides, Gross and Meienhofer (eds.), Academic Press, New York, 1–284 (1979), each incorporated herein by reference. The active protein can be readily synthesized and then screened in screening assays designed to identify reactive peptides.

Alternatively, a variety of expression vector/host systems may be utilized to contain and express a human G-CSF analog coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), WI 38, BHK, HepG2, 3T3, RIN, MDCK, A549, PC12, K562 and 293 cells. Exemplary protocols for the recombinant expression of the protein are described herein below.

A yeast system may be employed to generate the human G-CSF analogs of the present invention. The coding region of the human G-CSF analog cDNA is amplified by PCR. A DNA encoding the yeast pre-pro-alpha leader sequence is amplified from yeast genomic DNA in a PCR reaction using one primer containing nucleotides 1–20 of the alpha mating factor gene and another primer complementary to nucleotides 255–235 of this gene [Kurjan and Herskowitz, Cell 30:933–943 (1982)]. The pre-pro-alpha leader coding sequence and human G-CSF analog coding sequence fragments are ligated into a plasmid containing the yeast alcohol dehydrogenase (ADH2) promoter, such that the promoter directs expression of a fusion protein consisting of the pre-pro-alpha factor fused to the mature human G-CSF analog polypeptide. As taught by Rose and Broach [Meth. Enz. 185:234–279, Goeddel (ed.), Academic Press, Inc., San Diego, Calif. (1990)], the vector further includes an ADH2 transcription terminator downstream of the cloning site, the yeast "2-micron" replication origin, the yeast leu-2d gene, the yeast REPI and REP2 genes, the E. coli beta-lactamase gene, and an E. coli origin of replication. The beta-lactamase and leu-2d genes provide for selection in bacteria and yeast, respectively. The leu-2d gene also facilitates increased copy number of the plasmid in yeast to induce higher levels of expression. The REP 1 and REP2 genes encode proteins involved in regulation of the plasmid copy number.

The DNA construct described in the preceding paragraph is transformed into yeast cells using a known method, e.g., lithium acetate treatment [Stearns et al., Meth. Enz. 185: 280–297 (1990)]. The ADH2 promoter is induced upon exhaustion of glucose in the growth media [Price et al., Gene 55:287 (1987)]. The pre-pro-alpha sequence effects secretion of the fusion protein from the cells. Concomitantly, the yeast KEX2 protein cleaves the pre-pro sequence from the mature human G-CSF analogs [Bitter et. al., *Proc. Natl. Acad. Sci. USA* 81:5330–5334 (1984)].

Alternatively, human G-CSF analogs may be recombinantly expressed in yeast using a commercially available expression system, e.g., the Pichia Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol.

The secreted human G-CSF analog is purified from the yeast growth medium by, e.g., the methods used to purify human G-CSF analog from bacterial and mammalian cell supernatants.

Alternatively, the cDNA encoding human G-CSF analogs may be cloned into the baculovirus expression vector pVL1393 (PharMingen, San Diego, Calif.). This human G-CSF analog-containing vector is then used according to the manufacturer's directions (PharMingen) to infect *Spodoptera frugiperda* cells in sF9 protein-free media and to produce recombinant protein. The protein is purified and concentrated from the media using a heparin-Sepharose column (Pharmacia, Piscataway, N.J.) and sequential molecular sizing columns (Amicon, Beverly, Mass.), and resuspended in PBS. SDS-PAGE analysis shows a single band and confirms the size of the protein, and Edman sequencing on a Proton 2090 Peptide Sequencer confirms its N-terminal sequence.

Alternatively, the human G-CSF analogs may be expressed in an insect system. Insect systems for protein expression are well-known to those of skill in the art. In one such system, *Autographa californica* nuclear polyhedrosis virus (AcNPV) is used as a vector to express foreign genes in *Spodoptera frugiperda* cells or in Trichoplusia larvae. The human G-CSF analog coding sequence is cloned into a nonessential region of the virus, such as the polyhedrin gene, and placed under control of the polyhedrin promoter. Successful insertion of human G-CSF analog will render the polyhedrin gene inactive and produce recombinant virus lacking coat protein coat. The recombinant viruses are then used to infect S. frugiperda cells or Trichoplusia larvae in which human G-CSF analog is expressed [Smith et al., *J. Virol.* 46: 584 (1983); Engelhard E K et al., *Proc. Natl. Acad. Sci. USA* 91: 3224–7 (1994)].

In another example, the DNA sequence encoding the mature form of the protein is amplified by PCR and cloned into an appropriate vector, for example, pGEX-3X (Pharmacia, Piscataway, N.J.). The pGEX vector is designed to produce a fusion protein comprising glutathione-S-transferase (GST), encoded by the vector, and a protein encoded by a DNA fragment inserted into the vector's cloning site. The primers for the PCR may be generated to include, for example, an appropriate cleavage site.

The recombinant fusion protein may then be cleaved from the GST portion of the fusion protein. The pGEX-3X/human G-CSF analog construct is transformed into *E. coli* XL-1 Blue cells (Stratagene, La Jolla Calif.), and individual transformants are isolated and grown. Plasmid DNA from individual transformants is purified and partially sequenced using an automated sequencer to confirm the presence of the desired human G-CSF analog encoding gene insert in the proper orientation.

While certain embodiments of the present invention contemplate producing the human G-CSF analog protein using synthetic peptide synthesizers and subsequent FPLC analysis and appropriate refolding of the cysteine double bonds, it is contemplated that recombinant protein production also may be used to produce the human G-CSF analog peptide compositions. For example, induction of the GST/human G-CSF analog fusion protein is achieved by growing the transformed XL-1 Blue culture at 37° C. in LB medium (supplemented with carbenicillin) to an optical density at wavelength 600 nm of 0.4, followed by further incubation for 4 hours in the presence of 0.5 mM Isopropyl P-D-Thiogalactopyranoside (Sigma Chemical Co., St. Louis Mo.).

The fusion protein, expected to be produced as an insoluble inclusion body in the bacteria, may be purified as follows. Cells are harvested by centrifugation; washed in 0.15 M NaCl, 10 mM Tris, pH 8, 1 mM EDTA; and treated with 0.1 mg/mL lysozyme (Sigma Chemical Co.) for 15 min. at room temperature. The lysate is cleared by sonication, and cell debris is pelleted by centrifugation for 10 min. at 12,000× g. The fusion protein-containing pellet is resuspended in 50 mM Tris, pH 8, and 10 mM EDTA, layered over 50% glycerol, and centrifuged for 30 min. at 6000× g. The pellet is resuspended in standard phosphate buffered saline solution (PBS) free of $Mg^{++}$ and $Ca^{++}$. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/human G-CSF analog fusion protein is produced in bacteria as a soluble protein, it may be purified using the GST Purification Module (Pharmacia Biotech).

The fusion protein may be subjected to digestion to cleave the GST from the mature human G-CSF analog protein. The digestion reaction (20–40 µg fusion protein, 20–30 units human thrombin [4000 U/mg (Sigma) in 0.5 mL PBS] is incubated 16–48 hrs. at room temperature and loaded on a denaturing SDS-PAGE gel to fractionate the reaction products. The gel is soaked in 0.4 M KCl to visualize the protein bands. The identity of the protein band corresponding to the expected molecular weight of the human G-CSF analog may be confirmed by partial amino acid sequence analysis using an automated sequencer (Applied Biosystems Model 473A, Foster City, Calif.).

Alternatively, the DNA sequence encoding the predicted mature human G-CSF analog protein may be cloned into a plasmid containing a desired promoter and, optionally, a leader sequence [see, e.g., Better et al., Science 240:1041–43 (1988)]. The sequence of this construct may be confirmed by automated sequencing. The plasmid is then transformed into *E. coli*, strain MC1061, using standard procedures employing $CaCl_2$ incubation and heat shock treatment of the bacteria (Sambrook et al., supra). The transformed bacteria are grown in LB medium supplemented with carbenicillin, and production of the expressed protein is induced by growth in a suitable medium. If present, the leader sequence will affect secretion of the mature human G-CSF analog protein and be cleaved during secretion.

The secreted recombinant protein is purified from the bacterial culture media by the method described herein below.

Mammalian host systems for the expression of the recombinant protein also are well-known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing, which cleaves a "prepro" form of the protein, may also be important for correct insertion, folding and/or function. Different host cells, such as CHO, HeLa, MDCK, 293, WI38, and the like, have specific cellular machinery and characteristic mechanisms for such post-translational activities, and may be chosen to ensure the correct modification and processing of the introduced foreign protein.

In a particularly preferred method of recombinant expression of the human G-CSF analog proteins of the present invention, 293 cells are co-transfected with plasmids containing the human G-CSF analog cDNA in the pCMV vector (5' CMV promoter, 3' HGH poly A sequence) and pSV2neo (containing the neo resistance gene) by the calcium phosphate method. Preferably, the vectors should be linearized with ScaI prior to transfection. Similarly, an alternative construct using a similar pCMV vector with the neo gene incorporated can be used. Stable cell lines are selected from single cell clones by limiting dilution in growth media containing 0.5 mg/mL G418 (neomycin-like antibiotic) for 10–14 days. Cell lines are screened for human G-CSF analog expression by ELISA or Western blot, and high-expressing cell lines are expanded for large scale growth.

It is preferable that the transformed cells are used for long-term, high-yield protein production and as such stable expression is desirable. Once such cells are transformed with vectors that contain selectable markers along with the desired expression cassette, the cells may be allowed to grow for 1–2 days in an enriched media before they are switched to selective media. The selectable marker is designed to confer resistance to selection, and its presence allows growth and recovery of cells that successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to methotrexate; gpt, that confers resistance to mycophenolic acid; neo, that confers resistance to the aminoglycoside, G418; also, that confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, β-glucuronidase and its substrate, GUS, and luciferase and its substrate, luciferin.

D. Protein Purification

It will be desirable to purify the human G-CSF analog proteins generated by the present invention. Protein purification techniques are well-known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography, polyacrylamide gel electrophoresis, and isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptide within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification, and whether or not the expressed protein or peptide exhibits a detectable activity.

Various techniques suitable for use in protein purification will be well-known to those of skill in the art. These include, for example, precipitation with ammonium sulphate, PEG, antibodies, and the like; heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed, utilizing an HPLC apparatus, will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/

PAGE [Capaldi et al., *Biochem. Biophys. Res. Comm.* 76:425 (1977)]. It will therefore be appreciated that under differing electrophoresis conditions, the apparent molecular weights of purified or partially purified expression products may vary.

One may optionally purify and isolate such G-CSF analogs from other components obtained in the process. Methods for purifying can be found in U.S. Pat. No. 5,849,883 (incorporated by reference herein). Other methods are well-known in the art (See, also, Souza, supra, each incorporated herein by reference). These documents describe specific exemplary methods for the isolation and purification of G-CSF compositions that may be useful in isolating and purifying the G-CSF analogs of the present invention. Given the disclosure of these patents, it is evident that one of skill in the art would be well aware of numerous purification techniques that may be used to purify G-CSF from a given source.

Also it is contemplated that a combination of anion exchange and immunoaffinity chromatography may be employed to produce purified G-CSF analog compositions of the present invention.

E. Vectors for Cloning, Gene Transfer and Expression

As discussed in the previous section, expression vectors are employed to express the human G-CSF analog polypeptide product, which can then be purified and used for the treatment of neutropenia. In other embodiments, expression vectors may be used in gene therapy applications to introduce the human G-CSF analog-encoding nucleic acids into cells in need thereof and/or to induce human G-CSF analog expression in such cells. The present section is directed to a description of the production of such expression vectors.

Expression requires that appropriate signals be provided in the vectors, which include various regulatory elements, such as enhancers/promoters from both viral and mammalian sources that drive expression of the genes of interest in host cells. Elements designed to optimize messenger RNA stability and translatability in host cells also are described. The conditions for the use of a number of dominant drug selection markers for establishing permanent, stable cell clones expressing the products also are provided, as is an element that links expression of the drug selection markers to expression of the polypeptide.

a. Regulatory Elements

Promoters and Enhancers.

Throughout this application, the term "expression construct" or "expression vector" is meant to include any type of genetic construct containing a nucleic acid coding for gene products in which part or all of the nucleic acid encoding sequence is capable of being transcribed. The transcript may be translated into a protein, but it need not be. In certain embodiments, expression includes both transcription of a gene and translation of mRNA into a gene product. The nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term "promoter" will be used herein to refer to a group of transcriptional control modules that are clustered around the initiation site for RNA polymerase II. Much of the thinking about how promoters are organized is derived from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter, the phosphoglycerol kinase promoter, and glyceraldehyde-3-phosphate dehydrogenase promoter, all of which are promoters well-known and readily available to those of skill in the art, can be used to obtain high-level expression of the coding sequence of interest. The use of other viral or mammalian cellular or bacterial phage promoters that are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. Several inducible promoter systems are available for production of viral vectors. One such system is the ecdysone system (Invitrogen, Carlsbad, Calif.), which is designed to allow regulated expression of a gene of interest in mammalian cells. It consists of a tightly-regulated expression mechanism that allows virtually no basal level expression of the transgene, but over 200-fold inducibility.

Another inducible system that would be useful is the Tet-Off™ or Tet-On™ system (Clontech, Palo Alto, Calif.), originally developed by Gossen and Bujard [Gossen and Bujard, *Proc. Natl. Acad. Sci. USA* 15;89(12):5547–51 (1992); Gossen et al., *Science* 268(5218):1766–9 (1995)].

In some circumstances, it may be desirable to regulate expression of a transgene in a gene therapy vector. For example, different viral promoters with varying strengths of activity may be utilized depending on the level of expression desired. In mammalian cells, the CMV immediate early promoter is often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters, such as from the E1A, E2A, or MLP region, AAV LTR, cauliflower mosaic virus, HSV-TK, and avian sarcoma virus.

Similarly, tissue specific promoters may be used to effect transcription in specific tissues or cells, so as to reduce potential toxicity or undesirable effects to non-targeted tissues. For example, promoters such as the PSA, probasin, prostatic acid phosphatase, or prostate-specific glandular kallikrein (hK2) may be used to target gene expression in the prostate.

In certain indications, it may be desirable to activate transcription at specific times after administration of the gene therapy vector. This may be done with such promoters as those that are hormone or cytokine regulatable. For example, in gene therapy applications where the indication is a gonadal tissue where specific steroids are produced or routed to, use of androgen- or estrogen-regulated promoters may be advantageous. Such promoters that are hormone-regulatable include MMTV, MT-1, ecdysone, and RuBisco. Other hormone-regulated promoters, such as those responsive to thyroid, pituitary, and adrenal hormones, are expected to be useful in the present invention. Cytokine and inflammatory protein responsive promoters that could be used include K and T Kininogen [Kageyama et al., *J. Biol. Chem.* 262(5):2345–51 (1987)], c-fos, TNF-alpha, C-reactive protein [Arcone et al., *Nucleic Acids Res.* 16(8): 3195–207 (1988)], haptoglobin [Oliviero et al., *EMBO J.* 6(7):1905–12 (1987)], serum amyloid A2, C/EBP alpha, IL-1, IL-6 [Poli and Cortese, *Proc. Natl. Acad. Sci. USA* 86(21):8202–6 (1989)], complement C3 [Wilson et al., *Mol. Cell Biol.* 10(12):6181–91 (1990)], IL-8, alpha-i acid glycoprotein [Prowse and Baumann, *Mol. Cell. Biol.* 8(1): 42–51 (1988)], alpha-i antitypsin, lipoprotein lipase [Zechner et al., *Mol. Cell. Biol.* 8(6):2394–401 (1988)], angiotensinogen [Ron et al., *Mol. Cell. Biol.* 11(5):2887–95 (1991)], fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), stromelysin (inducible by phorbol ester, interleukin-1 and EGF), alpha-2 macroglobulin and alpha-1 antichymotrypsin.

Other promoters that could be used according to the present invention include Lac-regulatable, heat (hyperthermia) inducible promoters, and radiation-inducible (e.g., EGR [Joki et al., *Hum. Gene Ther.* 6(12):1507–13 (1995)], alpha-inhibin, RNA pol III tRNA met, and other amino acid promoters, U1 snRNA [Bartlett et al., *Proc. Natl. Acad. Sci. USA* 20;93(17):8852–7 (1996)], MC-1, PGK, β-actin and α-globin. Many other promoters that may be useful are listed in Walther and Stein [*J. Mol. Med.* 74(7): 379–92 (1996)].

It is envisioned that any of the above promoters, alone or in combination with another, may be useful according to the present invention depending on the action desired. In addition, this list of promoters should not be construed to be exhaustive or limiting, and those of skill in the art will know of other promoters that may be used in conjunction with the promoters and methods disclosed herein.

Another regulatory element contemplated for use in the present invention is an enhancer. These are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization. Enhancers useful in the present invention are well-known to those of skill in the art and will depend on the particular expression system being employed [Scharf et al., *Results Probl. Cell. Differ.* 20: 125–62 (1994); Bittner et al., *Meth. Enzymol.* 153: 516–544 (1987)].

Polyadenylation Signals.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read-through from the cassette into other sequences.

IRES.

In certain embodiments of the invention, the use of internal ribosome entry site (IRES) elements is contemplated to create multigene, or polycistronic, messages. IRES elements are able to bypass the ribosome scanning model of 5' methylated Cap dependent translation and begin translation at internal sites [Pelletier and Sonenberg, *Nature* 334:320–325 (1988)]. IRES elements from two members of the picornavirus family (poliovirus and encephalomyocarditis) have been described (Pelletier and Sonenberg, 1988, supra), as well an IRES from a mammalian message [Macejak and Sarnow, *Nature* 353:90–94 (1991)]. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins, and selectable markers. In this way, the expression of several proteins can be simultaneously engineered into a cell with a single construct and a single selectable marker.

b. Delivery of Expression Vectors

There are a number of ways in which expression vectors may be introduced into cells. In certain embodiments of the invention, the expression construct comprises a virus or engineered construct derived from a viral genome. In other embodiments, non-viral delivery is contemplated. The ability of certain viruses to enter cells via receptor-mediated endocytosis, to integrate into host cell genome, and express viral genes stably and efficiently have made them attractive candidates for the transfer of foreign genes into mammalian cells [Ridgeway, In: *Vectors: A survey of molecular cloning vectors and their uses*, Rodriguez & Denhardt (eds.), Stoneham: Butterworth, 467–492, 1988; Nicolas and Rubenstein, In: *Vectors: A survey of molecular cloning vectors and their uses*, Rodriguez & Denhardt (eds.), Stoneham: Butterworth, 493–513, 1988; Baichwal and Sugden, In: *Gene Transfer*, Kucherlapati (ed.), New York, Plenum Press, 117–148, 1986; Temin, In: *Gene Transfer*, Kucherlapati (ed.), New York: Plenum Press, 149–188, 1986)]. The first viruses used as gene vectors were DNA viruses including the papovaviruses (simian virus 40, bovine papilloma virus, and polyoma) (Ridgeway, 1988, supra; Baichwal and Sugden, 1986, supra) and adenoviruses (Ridgeway, 1988, supra; Baichwal and Sugden, 1986, supra). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988,supra; Temin, 1986, supra).

It is now widely recognized that DNA may be introduced into a cell using a variety of viral vectors. In such embodiments, expression constructs comprising viral vectors containing the genes of interest may be adenoviral (see, for example, U.S. Pat. Nos. 5,824,544; 5,707,618; 5,693,509; 5,670,488; 5,585,362; each incorporated herein by reference), retroviral (see for example, U.S. Pat. Nos. 5,888,502; 5,830,725; 5,770,414; 5,686,278; 4,861,719; each incorporated herein by reference), adeno-associated viral (see for example, U.S. Pat. Nos. 5,474,935; 5,139,941; 5,622,856; 5,658,776; 5,773,289; 5,789,390; 5,834,441; 5,863,541; 5,851,521; and 5,252,479; each incorporated herein by reference), an adenoviral-adenoassociated viral hybrid (see, for example, U.S. Pat. No. 5,856,152, incorporated herein by reference) or a vaccinia viral or a herpes viral (see, for example, U.S. Pat. Nos. 5,879,934; 5,849,571; 5,830,727; 5,661,033; and 5,328,688; each incorporated herein by reference) vector.

There are a number of alternatives to viral transfer of genetic constructs. This section provides a discussion of methods and compositions of non-viral gene transfer. DNA constructs of the present invention are generally delivered to a cell, and in certain situations, the nucleic acid or the protein to be transferred may be transferred using non-viral methods.

Several non-viral methods for the transfer of expression constructs into cultured mammalian cells are contemplated by the present invention. These include calcium phosphate precipitation [Graham and Van Der Eb, *Virology* 52:456–467 (1973); Chen and Okayama, *Mol. Cell. Biol.* 7:2745–2752 (1987); Rippe et al., *Mol. Cell. Biol.* 10:689–695 (1990)], DEAE-dextran [Gopal, *Mol. Cell. Biol.*, 5:1188–1190 (1985)], electroporation [Tur-Kaspa et al., *Mol. Cell. Biol.* 6:716–718 (1986); Potter et al., *Proc. Natl. Acad. Sci. USA* 81:7161–7165 (1984)], direct microinjection [Harland and Weintraub, *J. Cell Biol.* 101:1094–1099 (1985)], DNA-loaded liposomes [Nicolau and Sene, *Biochim. Biophys. Acta.* 721:185–190 (1982); Fraley et al., *Proc. Natl. Acad. Sci. USA* 76:3348–3352 (1979); Felgner, *Sci. Am.* 276(6):102–106 (1997); Felgner, *Hum. Gene Ther.* 7(15):1791–3 (1996)], cell sonication [Fechheimer et al., *Proc. Natl. Acad. Sci. USA* 84:8463–8467 (1987)], gene bombardment using high velocity microprojectiles [Yang et al., *Proc. Natl. Acad. Sci. USA* 87:9568–9572 (1990)], and receptor-mediated transfection [Wu and Wu, *J. Biol. Chem.* 262:4429–4432 (1987); Wu and Wu, *Biochem.*, 27:887–892 (1988); Wu and Wu, *Adv. Drug Deliv. Rev.* 12:159–167 (1993)].

Once the construct has been delivered into the cell, the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement), or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of, or in synchronization with, the host cell cycle. How the expression construct is delivered to a cell, and where in the cell the nucleic acid remains, is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers [Ghosh and Bachhawat, In: *Liver diseases targeted diagnosis and therapy using specific receptors and ligands*, Wu & Wu (ed.), New York: Marcel Dekker, pp. 87–104 (1991)]. The addition of DNA to cationic liposomes causes a topological transition from liposomes to optically birefringent liquid-crystalline condensed globules [Radler et al., *Science* 275 (5301):810–4 (1997)]. These DNA-lipid complexes are potential non-viral vectors for use in gene therapy and delivery.

Liposome-mediated nucleic acid delivery and expression of foreign DNA in vitro has been very successful. Also contemplated in the present invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA [Kaneda et al., *Science* 243:375–378 (1989)]. In other embodiments, the liposome may be complexed or employed in conjunction with nuclear non-histone chromosomal proteins (HMG-1) [Kato et al., *J. Biol. Chem.* 266:3361–3364 (1991)]. In yet further embodiments, the liposome may be complexed or employed in conjunction with both HVJ and HMG-1. In that such expression constructs have been successfully employed in transfer and expression of nucleic acid in vitro and in vivo. Then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993, supra).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987, supra) and transferrin [Wagner et al., *Proc. Natl. Acad. Sci. USA* 87(9):3410–3414 (1990)]. Recently, a synthetic neoglycoprotein, which recognizes the same receptor as ASOR, has been used as a gene delivery vehicle [Ferkol et al., *FASEB J.* 7:1081–1091 (1993); Perales et al., *Proc. Natl. Acad. Sci. USA* 91:4086–4090 (1994)] and epidermal growth factor (EGF) has also been used to deliver genes to squamous carcinoma cells (Myers, EPO 0273085).

In other embodiments, the delivery vehicle may comprise a ligand and a liposome. For example, Nicolau et al. [*Methods Enzymol.* 149:157–176 (1987)] employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a particular cell type by any number of receptor-ligand systems with or without liposomes.

In another embodiment of the invention, the expression construct may simply consist of naked recombinant DNA or plasmids. Transfer of the construct may be performed by any of the methods mentioned above that physically or chemically permeabilize the cell membrane. This is applicable, particularly for transfer in vitro; however, it may be applied for in vivo use as well. Dubensky et al. [*Proc. Nat. Acad. Sci. USA* 81:7529–7533 (1984)] successfully injected polyomavirus DNA in the form of $CaPO_4$ precipitates into liver and spleen of adult and newborn mice demonstrating active viral replication and acute infection. Benvenisty and Neshif [*Proc. Natl. Acad. Sci. USA* 83:9551–9555 (1986)] also demonstrated that direct intraperitoneal injection of $CaPO_4$-precipitated plasmids results in expression of the transfected genes.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them [Klein et al., *Nature* 327:70–73 (1987)]. Several devices for accelerating small particles have been developed. One such device relies on a high voltage discharge to generate an electrical current, which in turn provides the motive force [Yang et al., *Proc. Natl. Acad. Sci. USA* 87:9568–9572 (1990)]. The microprojectiles used have consisted of biologically inert substances such as tungsten or gold beads.

F. Methods of Treating Neutropenia

As mentioned herein above, it is contemplated that certain human G-CSF analogs or the vectors comprising polynucleotides encoding such proteins will be employed in replacement therapy protocols for the treatment of neutropenia. G-CSF has been found to be useful in the treatment of various conditions, where an increase in neutrophils will provide benefits. For example, for cancer patients, G-CSF is beneficial as a means of selectively stimulating neutrophil production to compensate for hematopoietic deficits resulting from chemotherapy or radiation therapy. Other indications include treatment of various infectious diseases and related conditions, such as sepsis, which is typically caused by a metabolite of bacteria. G-CSF is also useful alone, or in combination with other compounds, such as other cytokines, for growth or expansion of cells in culture (for example, for bone marrow transplants or ex vivo expansion). G-CSF has been administered to transplant patients as an adjunct to treatment of infection or for treatment of neutropenia.

a. Protein-Based Therapy

One of the therapeutic embodiments of the present invention is the provision, to a subject in need thereof, compositions comprising the human G-CSF analogs of the present invention. As discussed above, the proteins may have been generated through recombinant means or by automated peptide synthesis. The human G-CSF analog formulations for such a therapy may be selected based on the route of administration and may include liposomal formulations as well as classic pharmaceutical preparations.

The human G-CSF analog proteins are formulated into appropriate preparation and administered to one or more sites within the subject in a therapeutically-effective amount. In particularly preferred embodiments, the human G-CSF analog protein-based therapy is effected continuous or intermittent intravenous administration. By "therapeutically-effective amount" the present invention refers to that amount of a human G-CSF analog that is sufficient to support an observable change in the level of one or more biological activities of G-CSF. The change may be either an increase level of G-CSF activity. Preferably, the change is an increase in neutrophil proliferation.

Those of skill in the art will understand that the amounts of human G-CSF analog for therapeutic use may vary. It is contemplated that the specific activity of the human G-CSF analog protein preparation may be in the range of about 100 units/mg of protein to about 500 units/mg protein. Thus, a given preparation of a human G-CSF analog may comprise about 100 units/mg protein, about 125 units/mg protein, about 150 units/mg protein, about 175 units/mg protein, about 200 units/mg protein, about 225 units/mg protein, about 250 units/mg protein, about 275 units/mg protein, about 300 units/mg protein, about 325 units/mg protein, about 350 units/mg protein, about 375 units/mg protein, about 400 units/mg protein, about 425 units/mg protein, about 450 units/mg protein, about 475 units/mg protein and about 500 units/mg protein. A particularly preferred range is from about 100 units/mg protein to about 200 units/mg protein; a more preferable range is between about 150 to about 200 units/mg protein. Preferably, the protein composition is substantially free of contaminating factors, contamination level of less than 0.02% (w/w). Human G-CSF analog compositions, suitable for injection into a patient, can be prepared, for example, by reconstitution with a pharmacologically acceptable diluent of a lyophilized sample comprising purified human G-CSF analog and stabilizing salts.

Administration of the compositions can be systemic or local, and may comprise a single site injection of a therapeutically-effective amount of the human G-CSF analog protein composition. Any route known to those of skill in the art for the administration of a therapeutic composition of the invention is contemplated including, for example, intravenous, intramuscular, subcutaneous or a catheter for long-term administration. Alternatively, it is contemplated that the therapeutic composition may be delivered to the patient at multiple sites. The multiple administrations may be rendered simultaneously or may be administered over a period of several hours. In certain cases, it may be beneficial to provide a continuous flow of the therapeutic composition. Additional therapy may be administered on a period basis, for example, daily, weekly, or monthly.

b. Combination Therapy

In addition to therapies based solely on the delivery of the human G-CSF analogs, combination therapy is specifically contemplated. In the context of the present invention, it is contemplated that the human G-CSF analog therapy could be used similarly in conjunction with other agents commonly used for the treatment of neutropenia.

To achieve the appropriate therapeutic outcome, using the methods and compositions of the present invention, one would generally provide a composition comprising the human G-CSF analog and at least one other therapeutic agent (second therapeutic agent). In the present invention, it is contemplated that the second therapeutic agent may involve the administration or inclusion of at least one additional factor selected from among EPO, G-CSF, M-GDF, SCF, GM-CSF, M-CSF, CSF-1, IL-1, IL-2, IL-3, IL-4, IL-5, IL-6, IL-7, IL-8, IL-9, IL-10, IL-11, IL-12, or other various interleukins, IGF-1, LIF, interferon (such as a, B, gamma or consensus), neurotrophic factors (such as BDNF, NT-3, CTNF or noggin), other multi-potent growth factors (such as, to the extent these are demonstrated to be such multi-potent growth factors, flt-3/flk-2 ligand, stem cell proliferation factor, and totipotent stem cell factor), fibroblast growth factors (such as FGF), and analogs, fusion molecules, or other derivatives of the above. For example, G-CSF in combination with SCF has been found to mobilize peripheral blood progenitor cells in vivo. Ex vivo, for example, G-CSF in combination with SCF, IL-3 and IL-6 has been found useful for expansion of peripheral blood cells. Likewise, the present G-CSF analogs will provide for similar uses.

The combination therapy compositions would be provided in a combined amount effective to produce the desired therapeutic outcome in the treatment of neutropenia. This process may involve contacting the cells with the human G-CSF analog and the second agent(s) or factor(s) at the same time. This may be achieved by administering a single composition or pharmacological formulation that includes both agents, or by administering two distinct compositions or formulations, at the same time, wherein one composition includes the human G-CSF analog therapeutic composition and the other includes the second therapeutic agent.

Alternatively, the human G-CSF analog treatment may precede or follow the other agent treatment by intervals ranging from minutes to weeks. In embodiments where the second therapeutic agent and the human G-CSF analog are administered separately, one would generally ensure that a significant period of time did not expire between the time of each delivery, such that the second agent and the human G-CSF analog would still be able to exert an advantageously combined effect. In such instances, it is contemplated that one would administer both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Systemic delivery of human G-CSF analog expression constructs or proteins to patients may be a very efficient method for delivering a therapeutically effective gene to counteract the immediate clinical manifestations of the disease. Alternatively, local delivery of the human G-CSF analog and/or the second therapeutic agent may be appropriate in certain circumstances.

G. Assays for Determining G-CSF Analog Activity and Binding

In certain aspects of the present invention, it may be necessary to determine the activity of human G-CSF analog. In particular, the effect of the therapeutic compositions of the present invention on neutropenia may need to be monitored. Those of skill in the art are aware of numerous assays to determine G-CSF activity, some of which are described in the present section. This is by no means intended to be an exhaustive list of such assays and is merely intended to provide certain exemplary assays well-known to those of skill in the art that may be used in determining the G-CSF activity of the present invention. Further, the present section also describes assays for the determination of G-CSF binding to its receptor. Exemplary in vitro and in vivo assays for determining these activities are provided herein below.

a. In Vitro Assays

Cellular Proliferation Assays.

Cellular proliferation assays, some of which are described herein, are used to determine G-CSF analog effect on inducing cellular proliferation. Many assays are well-known in the art and some of these assays are described as follows.

Cell Counting.

Cells are passaged into supplemented MEMα medium (without G-CSF) 24 h prior to the initiation of the cell proliferation experiment, at which point parallel flasks of cells at a density of $10^5$ cells/mL are incubated in MEMA medium with 125 pM wild-type G-CSF or G-CSF analogs. Cell growth in each flask is measured on days 2, 5, and 8 as follows. Briefly, cells are diluted in an isotonic solution (ISOTON II, Coulter Diagnostics, Hialeah, Fla.), and counted in a Coulter counter (Coulter Electronics, Hialeah, Fla.).

$^3$H-Thymidine Incorporation.

This assay is based upon the incorporation of labeled $^3$H-thymidine into newly synthesized DNA of cells upon cell division. Some researchers also use the thymidine analogue 5-bromo-2'-deoxyuridine (BrdU) instead of [$^3$H]-thymidine in proliferation assays. Briefly, cells are passaged into supplemented MEMα medium (without G-CSF) 24 hr prior to the initiation of the cellular proliferation experiment, at which point parallel wells/flasks of cells at a density of $10^5$ cells/mL are incubated in MEMA medium with 125 pM wild-type G-CSF or G-CSF analogs. $^3$H-thymidine is added to the cell culture 12–24 hr prior to counting (termination of the experiment), and at the end of the assay the amount of radioactive incorporation in the DNA is measured in a liquid scintillation counter. Details of this method are well-known to one skilled in the art.

MTT.

MTT is used for the quantitative determination of cellular proliferation and activation e.g. in response to growth factors and cytokines. It is also used for the quantification of antiproliferative or cytotoxic effects e.g. mediated by tumor necrosis factor-α or -β and for the measurement of interferon action. The assay is based on the cleavage of the yellow tetrazolium salt, MTT, to purple formazan crystals by metabolic active cells. These salt crystals are insoluble in aqueous solution, but may be solubilized by adding the solubilization solution included in the kit and incubating the plates overnight in humidified atmosphere (e.g. 37° C., 6.5% CO 2). The solubilized formazan product is spectrophotometrically quantified using an ELISA reader. An increase in number of living cells results in an increase in the total metabolic activity in the sample. This increase directly correlates to the amount of purple formazan crystals formed, as monitored by the absorbance. Commercial MTT assay can be purchased from Roche Diagnostics (Indianapolis, Ind.).

Ligand Depletion Assay.

Ligand depletion for each protein is measured over time as described herein. As in the above experiments, G-CSF-dependent (OCI/AML1) cells are passaged into supplemented MEMα medium (without G-CSF) 24 h prior to the initiation of the ligand depletion experiments, at which point parallel flasks of cells at a density of $10^5$ cells/mL are incubated in MEMα medium with 125 pM wild-type G-CSF or G-CSF analog. After 24 h, the cell number in each flask is measured, as described above, and an aliquot of each medium supernatant, obtained after centrifugation to pellet cellular debris, is stored at −20° C. for measurement of G-CSF concentration. This is repeated every 24 h for eight days. The concentrations of G-CSF in the medium supernatant samples are then quantitated using enzyme-linked immunosorbent assay (ELISA) kits obtained from R&D Systems (Minneapolis, Minn.).

Internalization and Recycling Experiments.

Internalization experiments are performed over a time period of 5 min., similarly to published work [Kuwabara et al., *Amer. J. Physiol. Endocrinol. Metabol.* 32: E1–E9 (1995)]. Briefly, $10^8$ cells are washed twice with PBS and then incubated on ice in labeled ligand for 30 min. to obtain surface complexes. The cells are again washed twice with ice-cold PBS and resuspended in MEMα at 37° C. at t=0. The change in surface complexes and internal complexes is followed for a time period of 5 min.; a plot of internal complexes versus the time integral of surface complexes yields a linear relationship, the slope of which is the complex internalization rate constant [Wiley et al., *J. Biol. Chem.* 257: 4222–4229 (1982)]. Recycling experiments are performed identically to internalization experiments, except over a time period of 25 min. Data from recycling experiments are parameter fitted to obtain recycling rate constants.

Binding Assays.

Molecular binding assays, some of which are described herein, are used to assess G-CSF analog binding to G-CSFR. These in vitro and cell-based assays are described as follows.

BIACORE.

Ligand binding affinity of G-CSF analog to G-CSF receptor is measured using a BIAcore®2000 (BIAcore, Inc., Piscataway, N.J.). Histidine-tagged wild-type G-CSF is immobilized on the chip surface, and free receptor (~0.25–10 nM) is passed over the chip to generate a standard equilibrium curve and to calculate wild-type binding affinity using a 1:1 binding model. To determine each mutant binding affinity, 2 nM free receptor is mixed with a known concentration of mutant ligand and passed over the chip. Mutant equilibrium binding affinities are determined, using a 1:1 binding model with competition. Binding affinity data is analyzed using BIA evaluation 3.1 software (BIAcore, Inc.); and equilibrium dissociation constants ($K_D$) are determined.

ELISA.

Binding of G-CSF mutant analogs to G-CSFR is measured in an ELISA format competition assay. In this assay, G-CSFR is captured with the non-neutralizing G-CSF receptor antibody LMM741 (PharMingen, San Diego, Calif.) per manufacturer's protocol. Analog proteins are then assayed for their ability to compete with HRP-labeled G-CSF for receptor binding.

b. In Vivo Assays

Before the human G-CSF analog compositions of the present invention are employed in human therapeutic protocols, it may be desirable to monitor the effects of such compositions in animal models. There are a number of animal models that may be used in in vivo assays, known to those of skill in the art, that may be useful in the present invention.

In order to determine the efficacy of the human G-CSF analog protein and gene therapy compositions of the present invention, such animals may be injected intramuscularly and/or intravenously with the compositions of the present invention, and the ability to stimulate neutrophil proliferation in the presence and absence of the compositions may be determined. Such determinations will be helpful in providing guidance on the dosages and times of administration and the efficacy of a given composition against neutropenia. In gene therapy protocols, immunofluorescent staining of sections, obtained from biopsied muscle, may be performed, and expression of the human G-CSF analog in the transduced muscle fibers may be determined.

H. Pharmaceutical Compositions

The present invention also comprehends pharmaceutical compositions comprising effective amounts of polypeptide products of the invention together with pharmaceutically acceptable diluents, preservatives, solubilizers, emulsifiers, adjuvants and/or carriers useful in G-CSF therapy. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., thimersol, benzyl alcohol), and bulking substances (e.g., lactose, mannitol); incorporation of the material into particulate preparations of polymeric compounds, such as polylactic acid, polyglycolic acid, etc., or in association with liposomes. Such compositions will influence the physical state, stability, rate of in vivo release, and rate of in vivo clearance of the present G-CSF analogs. See, e.g., *Remington's Pharmaceutical Sciences,* 18th Ed. (1990) Mack Publishing Co., Easton, Pa., pages 1435–1712, which are herein incorporated by reference.

Derivatives of the present G-CSF analogs are also comprehended herein. Such derivatives include molecules modified by one or more water soluble polymer molecules, such as polyethylene glycol, or by the addition of polyamino acids, including fusion proteins (procedures for which are well-known in the art). Such derivatization may occur singularly at the N- or C-terminus or there may be multiple sites of derivatization. Substitution of one or more amino acids with lysine may provide additional sites for derivatization. (See U.S. Pat. No. : 5,824,784 and U.S. Pat. No. : 5,824,778, incorporated by reference herein).

The present analogs or derivatives thereof may be formulated for injection, or oral, nasal, pulmonary, topical, or other types of administration as one skilled in the art will recognize. The formulation may be liquid or may be solid, such as lyophilized, for reconstitution.

In general, the present analogs (or derivatives thereof) will be useful in the same way that currently available G-CSFs are useful, except the present analogs provide enhanced cellular response (superagonist or G-CSF agonist activity). Such changes in cellular response occur by affecting G-CSF receptor binding and/or the processes of sorting, recycling and degradation via the ligand/receptor endocytic trafficking pathways.

These uses include the treatment of a variety of hematopoietic, neurological, and reproduction related conditions. Thus, the present compositions and methods for the manufacture of medicaments may be useful for the treatment of such conditions. Conditions alleviated or modulated by the administration of the present analogs are typically those characterized by a reduced hematopoietic or immune function and more specifically, a reduced neutrophil count. Such conditions may be induced as a course of therapy for other purposes, such as chemotherapy or radiation therapy. Such conditions may result from infectious disease, such as bacterial, viral, fungal, or other infectious disease. For example, sepsis results from bacterial infection. Or, such condition may be hereditary or environmentally caused, such as severe chronic neutropenia or leukemias. Age may also play a factor, as in the geriatric setting; patients may have a reduced neutrophil count or reduced neutrophil mobilization. Some of such conditions are reviewed in Filgrastim (r-metHuG-CSF) In: *Clinical Practice*, Morstyn and Dexter (eds.), Marcel Dekker, Inc., New York (1993), p.351. Other less-studied conditions which may be alleviated or modulated by the administration of the present analogs may include the reduction of lipids (or cholesterol) in the blood stream and certain cardiovascular conditions, as G-CSF may induce the production of plasminogen activators. In addition, the present G-CSF analog compositions may be used for mobilization of peripheral blood progenitor cells.

The present G-CSF analogs (or derivative compositions) may also be used in vitro. For example, in a gene therapy setting, one may desire to transfect a hematopoietic cell with exogenous DNA, and culture said cell using the present G-CSF analog formulations. Thus, in yet another aspect, the present invention involves a method for culturing hematopoietic cells in vitro comprised of: a) placing said cells in a suitable culture medium, said suitable culture medium containing a G-CSF analog composition according to the present invention, and b) providing suitable conditions for the growth of said hematopoietic cells.

More particularly, the present invention provides a method of transfecting hematopoietic cells with exogenous DNA comprising: a) culturing said hematopoietic cells with a G-CSF analog composition according to the present invention, and b) transfecting said cultured cells with exogenous DNA. The hematopoietic cells may be, for example, bone marrow cells or peripheral blood progenitor cells. In addition, other cells well-known to one skilled in the art can be used.

In order to prepare human G-CSF analog containing compositions for clinical use, it will be necessary to prepare the viral expression vectors, proteins, and nucleic acids as pharmaceutical compositions, i.e., in a form appropriate for in vivo applications. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the human G-CSF analog or an expression vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well-known in the art. Except insofar as any conventional media or agent is incompatible with the vectors or cells of the present invention, its use in therapeutic compositions is contemplated. Supplementary active ingredients also can be incorporated into the compositions.

The active compositions of the present invention include classic pharmaceutical preparations. Administration of these compositions according to the present invention will be via any common route so long as the target tissue is available via that route. The pharmaceutical compositions may be introduced into the subject by any conventional method, e.g., by intravenous, intradermal, intramusclar, intramammary, intraperitoneal, intrathecal, retrobulbar, intrapulmonary (e.g., term release); by oral, sublingual, nasal, anal, vaginal, or transdermal delivery, or by surgical implantation at a particular site. The treatment may consist of a single dose or a plurality of doses over a period of time.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents (for example, sugars or sodium chloride). Prolonged absorption of the injectable compositions can be brought about by the use in the compositions of agents delaying absorption (for example, aluminum monostearate and gelatin).

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques that yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients also can be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

Generally, an effective amount of the present G-CSF analogs (or derivatives) will be determined by the age, weight, and condition or severity of disease of the recipient. See, *Remington's Pharmaceutical Sciences*, supra, pages 697–773, herein incorporated by reference. Typically, a dosage of between about 0.001 µg/kg body weight/day to about 1000 µg/kg body weight/day, may be used, but more or less, as a skilled practitioner will recognize, may be used. Dosing may be one or more times daily, or less frequently, and may be in conjunction with other compositions as described herein. It should be noted that the present invention is not limited to the dosages recited herein.

"Unit dose" is defined as a discrete amount of a therapeutic composition dispersed in a suitable carrier. For example, where polypeptides are being administered parenterally, the polypeptide compositions are generally injected in doses ranging from 1 µg/kg to 100 mg/kg body weight/day, preferably at doses ranging from 0.1 mg/kg to about 50 mg/kg body weight/day. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. See, for example, *Remington's Pharmaceutical Sciences*, supra, pages 1435–1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

Appropriate dosages may be ascertained through the use of established assays for determining level of neutropenia in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

In gene therapy embodiments employing viral delivery, the unit dose may be calculated in terms of the dose of viral particles being administered. Viral doses include a particular number of virus particles or plaque forming units (pfu). For embodiments involving adenovirus, particular unit doses include $10^3$, $10^4$, $10^5$, $10^6$, $10^7$, $10^8$, $10^9$, $10^{10}$, $10^{11}$, $10^{12}$, $10^{13}$ or $10^{14}$ pfu. Particle doses maybe somewhat higher (10 to 100-fold) due to the presence of infection-defective particles.

It will be appreciated that the pharmaceutical compositions and treatment methods of the invention may be useful in fields of human medicine and veterinary medicine. Thus the subject to be treated may be a mammal, preferably human or other animal. For veterinary purposes, subjects include for example, farm animals including cows, sheep, pigs, horses and goats, companion animals such as dogs and cats, exotic and/or zoo animals, laboratory animals including mice, rats, rabbits, guinea pigs and hamsters; and poultry such as chickens, turkeys, ducks and geese.

In addition, the present invention contemplates a kit containing components for culturing bone marrow cells or peripheral blood progenitor cells comprised of: a) a G-CSF analog composition of the present invention; and b) components suitable for preparing medium for culturing bone marrow cells or peripheral blood progenitor cells.

I. Method of Screening G-CSF Analogs

The present invention relates a method for screening analogs of granulocyte-colony stimulating factor (G-CSF) for use as G-CSF replacements or G-CSF antagonists. This method comprises: determining the capacity of the G-CSF analog for binding to target cells and determining an equilibrium dissociation constant (Kd) for said analog; determining the capacity of the G-CSF analog for stimulating cellular proliferation (N) of target cells at a given ligand concentration (L); normalizing the N value obtained for the G-CSF analog with the corresponding N value for wild-type G-CSF at a given value of L to obtain Y-axis values; calculating the L/Kd values for the G-CSF analog and wild-type G-CSF to obtain X-axis values; plotting the normalized N value with the L/Kd values for the G-CSF analog and wild-type G-CSF; selecting as a G-CSF replacement, an analog displaying increased proliferation and either increased or decreased binding relative to wild-type G-CSF; and selecting as a G-CSF antagonist, an analog displaying decreased proliferation and either equal or increased binding relative to wild-type G-CSF. The cellular proliferation may be determined by any of several methods, for example, determining cell number (i.e., counting cells with a Coulter counter), measuring $^3$H-thymidine incorporation, measuring MTT incorporation, or other methods known in the art. The equilibrium dissociation constant (Kd) also may determined by any of several methods, for example, BIAcore analysis, ELISA, or other methods known in the art.

As utilized in accordance with the present disclosure, the following terms unless otherwise indicated, shall be understood to have the following meanings:

The term "determining" refers to establishing or ascertaining definitely, after consideration, investigation, or calculation.

The term "normalizing" refers to adjusting the representation of a quantity so that this representation lies within a prescribed range. In the present invention, cellular proliferation of the G-CSF analogs is normalized so that the wild-type G-CSF has a value of one at each concentration of ligand stimulation.

The term "calculating" refers to performing logical arithmetic operations based on numerical data.

Cell types used for screening the effects of the G-CSF analogs are well-known to one of skill in the art. These may preferably include, for example, bone marrow stem cells, neutrophil precursor cells, immortalized stem cells, acute myeloid leukemia cells.

J. EXAMPLES

The present invention is described in more detail with reference to the following non-limiting examples, which are offered to more fully illustrate the invention, but are not to be construed as limiting the scope thereof. The examples illustrate the preparation of the present G-CSF analogs and the testing of these analogs in vitro. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

Example 1

Experimental Materials and Cell Culture

Minimum essential medium alpha (MEMα), L-glutamine, penicillin-streptomycin, and fetal bovine serum (FBS) were obtained from Life Technologies, Inc. (Rockville, Md.). Isotonic solution for the Coulter counter (ISOTON II, Coulter Diagnostics, Hialeah, Fla.) was obtained from Curtin Matheson Scientific Inc. (Houston, Tex.).

The G-CSF-dependent suspension cell line, OCI/AML1, a generous gift from Ernest A. McCulloch [Ontario Cancer Institute (OCI), Princess Margaret Hospital, 610 University Avenue, Toronto, Ontario, M5G 2M9, Canada], was used for all experiments. Cells were routinely cultured in Corning 75-cm$^2$ tissue culture flasks in MEMα supplemented with 20% FBS, 200 mM L-glutamine, 100 units/mL penicillin, 100 g/mL streptomycin, and 270 pM G-CSF in a humidified atmosphere with 5% $CO_2$. Cells were passaged to $10^5$ cells/mL every 3 to 4 days.

Example 2

Method of Screening G-CSF Mutants

Presented below are data demonstrating G-CSF analogs resulting in an effect on cellular trafficking as compared to G-CSF or recombinant G-CSF having a methionine residue at position −1 ("metG-CSF") as noted in SEQ ID NO: 2. The effects from these modifications demonstrate advantages in stability which are not seen in other G-CSF species. In particular, these analogs provide enhanced cellular response (superagonist or G-CSF agonist type activity) or decreased cellular response (partial agonist activity if there is some response and the G-CSF receptor is not blocked, or antagonist activity if the G-CSF receptor is blocked) as compared to G-CSF or metG-CSF. Such changes in cellular response can occur by affecting G-CSF receptor binding and/or the processes of sorting, recycling and degradation via the ligand/receptor endocytic trafficking pathways.

G-CSF-dependent cells (OCI/AML1) were factor-starved for 24 hours and then incubated with G-CSF or G-CSF analogs (at an initial ligand concentration (L) of 1000, 500, 250, or 125 pM) at an initial cell density of $1\times10^5$ cells/mL. Media was not replaced during this time period. After seven days, cell number was measured using a Coulter counter. Methods used are well known in the art. See also Souza et al., "Recombinant Human Granulocyte Colony-Stimulating Factor: Effects On Normal And Leukemic Myeloid Cells," *Science*, 232(4746):61–5 (1986); U.S. Pat. No. 4,810,643 both incorporated by reference herein. In addition to the above cell proliferation assays, activity of the analogs can also be determined as noted in Souza et al., supra, or in U.S. Pat. No. 4,810,643 both incorporated by reference herein.

The ligand binding affinity of G-CSF analog to G-CSF receptor was measured using a BIAcore®2000 (BIAcore, Inc., Piscataway, N.J.). Histidine-tagged wild-type GCSF was immobilized on the chip surface, and free receptor (~0.25–10 nM) was passed over the chip to generate a standard equilibrium curve and to calculate wild-type binding affinity using a 1:1 model. To determine each mutant ligand binding affinity, 2 nM free receptor was mixed with a known concentration of mutant ligand and passed over the chip. Mutant equilibrium binding affinities were determined, using a 1:1 model with competition. Binding affinity data was analyzed using BIA evaluation 3.1 software (BIAcore, Inc.); and equilibrium dissociation constants ($K_D$) were determined.

Results are presented in FIG. 1, which exhibits a plot of cell proliferation after seven days of treatment with several G-CSF analogs. The cell proliferation of each analog was normalized to wild-type for four different initial concentrations of the ligand (L); 1000, 500, 250, and 125 pM. Thus, the spread along the x-axis is due to the differences in Kd for the analogs, not differences in L. A vertical dashed line on the plot has been included to divide the region into four quadrants, each of which helps to classify a given analog, based on its binding affinity and potency relative to wild-type G-CSF. The x-axis of the quadrant plot represents the initial ligand concentration (L) in relation to the equilibrium dissociation constant (Kd) for each analog, "L/Kd". Because the Kd for each analog is different, it results in the data being spread over a few orders of magnitude, even though L was the same in each case. The y-axis represents the cell number measured after seven days of ligand treatment, divided by the cell number of the control, after seven days with the same initial ligand concentration of wild-type G-CSF.

The bottom left quadrant represents decreased binding and decreased cellular proliferation compared to wild-type. The top left quadrant represents decreased binding but enhanced cellular proliferation. The bottom right quadrant represents relatively equal binding but decreased cellular proliferation. The top right quadrant represents relatively equal binding but enhanced cellular proliferation.

In particular, in the top right quadrant, [Ala$^{33}$]G-CSF (G32), [Glu$^{26}$]G-CSF(G33), [Asp$^{30}$]G-CSF(G35), [Leu$^{26}$]G-CSF(G36), [Ala$^{38}$]G-CSF(G37), and [Ala$^{26}$]G-CSF(G38) exhibited enhanced trafficking properties. These G-CSF analogs demonstrated roughly the same binding activity as wild-type (WT) and elicited roughly the same cellular proliferation at high ligand concentrations. At the x-axis where L/Kd equals approximately 10 (i.e., ligand concentration was in great excess relative to the Kd), there was a small difference in cellular proliferation between wild-type and [Ala$^{33}$]G-CSF (G32), [Glu$^{26}$]G-CSF(G33), [Asp$^{30}$]G-CSF(G35), [Leu$^{26}$]G-CSF(G36), [Ala$^{38}$]G-CSF(G37), and [Ala$^{26}$]G-CSF(G38). Since trafficking phenomena are not of great importance at such high ligand concentrations, the signaling strengths of these ligands can be inferred to be roughly the same. However, at the x-axis where L/Kd equals approximately 1 (and where trafficking phenomena and ligand depletion are important), there was a two-fold enhancement of cellular proliferation by [Ala$^{38}$]G-CSF (G37) and [Ala$^{26}$]G-CSF(G38) relative to wild-type (WT). Hence, [Ala$^{38}$]G-CSF(G37) and [Ala$^{26}$]G-CSF(G38) demonstrated enhanced trafficking properties over wild-type, and all of the aforementioned analogs in this quadrant could serve as G-CSF replacements.

In the top left quadrant, [Glu$^{50}$]G-CSF (G30) and [Glu$^{54}$]G-CSF (G31) exhibited enhanced signaling or reduced degradation through trafficking. [Glu$^{50}$]G-CSF (G30) and [Glu$^{54}$]G-CSF (G31) elicited decreased binding activity compared to wild-type (WT), but both analogs demonstrated enhanced cellular proliferation.

In the bottom right quadrant, [Ala$^{46}$]G-CSF (G08) demonstrated roughly the same binding activity as wild-type (WT); however, [Ala$^{46}$]G-CSF (G08) elicited decreased cellular proliferation. Hence, [Ala$^{46}$]G-CSF (G08) exhibited G-CSF receptor antagonistic activity, and thus may be useful as a G-CSF antagonist.

Finally, [Glu$^{144}$]G-CSF (G24), [Glu$^{41}$]G-CSF(G27), [Glu$^{47}$]G-CSF(G28), and [Ala$^{19}$]G-CSF(G34), plotted in the lower left quadrant. These analogs demonstrated decreased binding and decreased cellular proliferation compared to wild type. Therefore, these analogs would not likely serve as G-CSF replacements.

The right y-axis displays a key for the tested mutant analogs (G08=[Ala$^{46}$]G-CSF, G24=[Glu$^{144}$]G-CSF, G27=[Glu$^{41}$]G-CSF, G28=[Glu$^{47}$]G-CSF, G30=[Glu$^{50}$]G-CSF, G31=[Glu$^{54}$]G-CSF, G32=[Ala$^{33}$]G-CSF, G33=[Glu$^{26}$]G-CSF, G34=[Ala$^{19}$]G-CSF, G35=[Asp$^{30}$]G-CSF, G36=[Leu$^{26}$]G-CSF, G37=[Ala$^{38}$]G-CSF, G38=[Ala$^{26}$]G-CSF, WT=wild type, and PEG [pegylated wild type (SD/01) (wild type G-CSF covalently modified with polyethylene glycol subunits)].

Example 3

Preparation and Characterization of G-CSF Analogs

G-CSF analogs were prepared by either insertional or site-directed mutagenesis of DNA encoding r-met-HuG-CSF using the PCR overlap extension method [Aiyar et al., *Meth. Mol. Biol.* 57:177–191 (1996)]. After confirming mutations by sequence analysis, each of the mutants was expressed in *Escherichia coli* K12, refolded, and purified as described in [Lu et al., *J. Biol. Chem.* 267:8770–8777 (1992)]. For protocols and procedures see also "Recombinant PCR," Russell Higuchi, in *PCR Protocols*, Michael A. Innis, David H. Gelfand, John J. Sninsky and Thomas J. White eds. Academic Press, Inc., San Diego, Calif., 1990; and "Site directed mutagenesis of cloned DNA" in *Molecular Cloning, A Lab Manual* J. Sambrook, E. F. Fritsch and T. Maniatis, eds. Cold Spring Harbor Press, CSH, N.Y., 1989 (both incorporated by reference herein). The *E. coli* expression of r-met-HuG-CSF was previously reported. (U.S. Pat. No. 4,810,643 and 5,849,883, both incorporated herein by reference.). The DNA encoding recombinant human G-CSF had an initial methionine codon followed by codons for the 174 amino acid species of human G-CSF. The purified r-met-HuG-CSF analogs retain the initiating Met (position Met −1).

Confirmation of the identity of the G-CSF analogs of the present invention was accomplished by N-terminal amino acid sequencing of intact proteins. Sequences of the purified G-CSF analogs matched the sequences predicted from the respective DNA sequences. Such methods are well known in the art [Shively, J. E., "The Chemistry of Protein Sequence Analysis" *EXS* 88:99–117 (2000)].

While the present invention has been described in terms of preferred embodiments, it is understood that variations and modifications will occur to those skilled in the art. Therefore, it is intended that the appended claims cover all such equivalent variations which come within the scope of the invention as claimed.

We claim:

1. A method for screening analogs of Granulocyte Colony Stimulating Factor (G-CSF) for use as G-CSF replacements, said method comprising:

a.) determining the capacity of the G-CSF analog for binding to target cells and determining an equilibrium dissociation constant (Kd) for said analog;

b.) determining the capacity of the G-CSF analog for stimulating cellular proliferation (N) of target cells at a given initial ligand concentration (L);

c.) normalizing the N value obtained for the G-CSF analog with the corresponding N value for wild-type G-CSF at a given value of L to obtain Y-axis values;

d.) calculating the L/Kd values for the G-CSF analog and wild-type G-CSF to obtain X-axis values;

e.) plotting the normalized N value with the UKd values for the G-CSF analog and wild-type G-CSF; and f.) selecting as a G-CSF replacement, an analog displaying increased proliferation and either increased or decreased binding relative to wild-type G-CSF.

2. A method for screening analogs of G-CSF for use as G-CSF antagonists, said method comprising:

a.) determining the capacity of the G-CSF analog for binding to target cells and determining an equilibrium dissociation constant (Kd) for said analog;

b.) determining the capacity of the G-CSF analog for stimulating cellular proliferation (N) of target cells at a given initial ligand concentration (L);

c.) normalizing the N value obtained for the G-CSF analog with the corresponding N value for wild-type G-CSF at a given value of L to obtain Y-axis values;

d.) calculating the L/Kd values for the G-CSF analog and wild-type G-CSF to obtain X-axis values;

e.) plotting the normalized N value with the L/Kd values for the G-CSF analog and wild-type G-CSF; and f.) selecting as a G-CSF antagonist, an analog displaying decreased proliferation and either equal or increased binding relative to wild-type G-CSF.

3. The method of claims 1 or 2, wherein said target cell is a bone marrow stem cell, a neutrophil precursor cell, an immortalized stem cell, or an acute myeloid leukemia cell.

4. The method of claims 1 or 2, wherein cellular proliferation is assessed by determining cell number, measuring $^3$H-thymidine incorporation, or using an MTT assay.

5. The method of claims 1 or 2, wherein the equilibrium dissociation constant (Kd) is assessed by BIAcore analysis or ELISA.

* * * * *

SEQUENCE LISTING

<160> NUMBER OF SEQ ID NOS: 2

<210> SEQ ID NO 1
<211> LENGTH: 565
<212> TYPE: DNA
<213> ORGANISM: Homo sapiens
<220> FEATURE:
<221> NAME/KEY: CDS -continued

```
<222> LOCATION: (33)..(554)

<400> SEQUENCE: 1
tctagaaaaa accaaggagg taataaataa tg act cca tta ggt cct gct tct        53
                                   Thr Pro Leu Gly Pro Ala Ser
                                   1               5 tct ctg ccg caa agc ttt ctg ctg aaa tgt ctg gaa cag gtt cgt aaa       101
Ser Leu Pro Gln Ser Phe Leu Leu Lys Cys Leu Glu Gln Val Arg Lys
        10                  15                  20 atc cag ggt gac ggt gct gca ctg caa gaa aaa ctg tgc gct act tac       149
Ile Gln Gly Asp Gly Ala Ala Leu Gln Glu Lys Leu Cys Ala Thr Tyr
 25                  30                  35 aaa ctg tgc cat ccg gaa gaa ctg gta ctg ctg ggt cat tct ctt ggg       197
Lys Leu Cys His Pro Glu Glu Leu Val Leu Leu Gly His Ser Leu Gly
 40                  45                  50                  55 atc ccg tgg gct ccg ctg tct tct tgc cca tct caa gct ctt cag ctg       245
Ile Pro Trp Ala Pro Leu Ser Ser Cys Pro Ser Gln Ala Leu Gln Leu
                 60                  65                  70 gct ggt tgt ctg tct caa ctg cat tct ggt ctg ttc ctg tat cag ggt       293
Ala Gly Cys Leu Ser Gln Leu His Ser Gly Leu Phe Leu Tyr Gln Gly
             75                  80                  85 ctt ctg caa gct ctg gaa ggt atc tct ccg gaa ctg ggt ccg act ctg       341
Leu Leu Gln Ala Leu Glu Gly Ile Ser Pro Glu Leu Gly Pro Thr Leu
         90                  95                 100 gac act ctg cag cta gat gta gct gac ttt gct act act att tgg caa       389
Asp Thr Leu Gln Leu Asp Val Ala Asp Phe Ala Thr Thr Ile Trp Gln
    105                 110                 115 cag atg gaa gag ctc ggt atg gca cca gct ctg caa ccg act caa ggt       437
Gln Met Glu Glu Leu Gly Met Ala Pro Ala Leu Gln Pro Thr Gln Gly
120                 125                 130                 135 gct atg ccg gca ttc gct tct gca ttc cag cgt cgt gca gga ggt gta       485
Ala Met Pro Ala Phe Ala Ser Ala Phe Gln Arg Arg Ala Gly Gly Val
                140                 145                 150 ctg gtt gct tct cat ctg caa tct ttc ctg gaa gta tct tac cgt gtt       533
Leu Val Ala Ser His Leu Gln Ser Phe Leu Glu Val Ser Tyr Arg Val
            155                 160                 165 ctg cgt cat ctg gct cag ccg taatagaatt c                              565
Leu Arg His Leu Ala Gln Pro
        170

<210> SEQ ID NO 2
<211> LENGTH: 174
<212> TYPE: PRT
<213> ORGANISM: Homo sapiens

<400> SEQUENCE: 2

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
```

-continued

```
        100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```